US010160746B2

(12) United States Patent
Alisi et al.

(10) Patent No.: US 10,160,746 B2
(45) Date of Patent: *Dec. 25, 2018

(54) 1H-INDAZOLE-3-CARBOXAMIDE COMPOUNDS AS GLYCOGEN SYNTHASE KINASE 3 BETA INHIBITORS

(71) Applicant: AZIENDE CHIMICHE RIUNITE ANGELINI FRANCESCO A.C.R.A.F. S.P.A., Rome (IT)

(72) Inventors: Maria Alessandra Alisi, Rome (IT); Nicola Cazzolla, Albano Laziale (IT); Patrizia Dragone, Rome (IT); Guido Furlotti, Rome (IT); Caterina Maugeri, Rome (IT); Rosella Ombrato, San Lorenzo del Vallo (IT); Francesca Mancini, Nettuno (IT)

(73) Assignee: AZIENDE CHIMICHE RIUNITE ANGELINI FRANCESCO A.C.R.A.F. S.p.A., Rome (IT)

( * ) Notice: Subject to any disclaimer, the term of this patent is extended or adjusted under 35 U.S.C. 154(b) by 0 days.

This patent is subject to a terminal disclaimer.

(21) Appl. No.: 15/439,172

(22) Filed: Feb. 22, 2017

(65) Prior Publication Data

US 2017/0157121 A1 Jun. 8, 2017

Related U.S. Application Data

(63) Continuation of application No. 14/373,100, filed as application No. PCT/EP2013/052400 on Feb. 7, 2013, now Pat. No. 9,611,249.

(30) Foreign Application Priority Data

Feb. 21, 2012 (EP) ..................... 12156292

(51) Int. Cl.
C07D 401/12 (2006.01)
C07D 401/14 (2006.01)
C07D 405/14 (2006.01)
C07D 413/14 (2006.01)
A61K 31/454 (2006.01)
A61K 31/4545 (2006.01)
A61K 31/506 (2006.01)

(52) U.S. Cl.
CPC .......... *C07D 401/12* (2013.01); *A61K 31/454* (2013.01); *A61K 31/4545* (2013.01); *A61K 31/506* (2013.01); *C07D 401/14* (2013.01); *C07D 405/14* (2013.01); *C07D 413/14* (2013.01)

(58) Field of Classification Search
CPC .................................................. A61K 31/454
See application file for complete search history.

(56) References Cited

U.S. PATENT DOCUMENTS

| | | | |
|---|---|---|---|
| 7,632,849 B2 | 12/2009 | Alisi et al. | |
| 8,455,519 B2 | 6/2013 | Alsi et al. | |
| 2006/0052417 A1 | 3/2006 | Alisi et al. | |
| 2006/0135589 A1 | 6/2006 | Berdino et al. | |
| 2011/0112161 A1 | 5/2011 | Bolin et al. | |

FOREIGN PATENT DOCUMENTS

WO 2005014554 A1 2/2005

OTHER PUBLICATIONS

Octavian "Symptomatic Treatment of Huntington Disease" Neurotherapeutics: The Journal of the American Society for Experimental NeuroTherapeutics Apr. 2008, vol. 5, 181-197.*
Cole "Glycogen synthase kinase 3 substrates in mood disorders and schizophrenia" FEBS Journal (2013), 280(21), 5213-522.*
Kozlovsky "Low GSK-3b in schizophrenia as a consequence of neurodevelopmental insult" European Neuropsychopharmacology (2005), 15(1), 1-11.*
Garson "Models of ovarian cancer—Are we there yet?" Molecular and Cellular Endocrinology 239 (2005) 15-26.*
Sale "Models of ovarian cancer metastasis: Murine models" Drug Discovery Today: Disease Models 2006, 3, 150-154.*
Schober "New Advances in the Treatment of Metastatic Pancreatic Cancer" Digestion 2015;92:175-184.*
Sanz-Garcia, "Current and advancing treatments for metastatic colorectal cancer" Expert Opinion on Biological Therapy, 16:1, 2016, 93-110.*
Chaichian "Targeted Therapies in Systemic Lupus Erythematosus: A State-of-the-Art Review" J Clin Cell Immunol 2013, S6, 1-8.*
Georg Pilz, "Modern multiple sclerosis treatment—what is approved, what is on the horizon" Drug Discovery Today Dec. 2008 , vol. 13, Nos. 23/24 1013-1025.*
Lutz "Overview of Animal Models of Obesity" Curr Protoc Pharmacol. Sep. 2012 ; Chapter: Unit 5.61. 1-22.*
Vickers "The utility of animal models to evaluate novel anti-obesity agents" British Journal of Pharmacology (2011) 164 1248-1262.*
DeWeerdt "Parkinson's disease 4 Big Questions" vol. 538, Oct. 2016, S17.*
Kalia "Parkinson's disease" Lancet 2015; 386: 896-912.*
Jackson-Lewis "Animal models of Parkinson's disease" Parkinsonism and Related Disorders 18S1 (2012) S183-S185.*
Konstantinos Makrilakis "Pathophysiology of Type 2 diabetes" Chapter 3 in Diabetes in Clinical Practice: Questions and Answers from Case Studies, Nicholas Katsilambros et al. eds. John Wiley & Sons: 2006, pp. 43-58.
Hook V. Y.H. "Neuroproteases in Peptide Neurotransmission and Neurodegenerative Diseases Applications to Drug Discovery Research" Biodrugs 2006, 20, 105-119.

(Continued)

*Primary Examiner* — David K O'Dell
(74) *Attorney, Agent, or Firm* — Oblon, McClelland, Maier & Neustadt, L.L.P.

(57) ABSTRACT

The present invention relates to the 1H-indazole-3-carboxamide compounds as glycogen synthase kinase 3 beta (GSK-3β) inhibitors and to their use in the treatment of GSK-3β-related disorders such as, for example, (i) insulin-resistance disorders; (ii) neurodegenerative diseases; (iii) mood disorders; (iv) schizophrenic disorders; (v) cancerous disorders; (vi) inflammation, (vii) substance abuse disorders; (viii) epilepsies; and (ix) neuropathic pain.

15 Claims, No Drawings

(56) References Cited

OTHER PUBLICATIONS

Tomohiro Chiba "Emerging Therapeutic Strategies in Alzheimer's Disease" Intech 2013, 181-226.
Jhee et al. "b-amyloid therapies in Alzheimer's disease" Expert Opinion on Investigational Drugs 2001, 10, 593-605.
Yuzwa "O-GlcNAc and neurodegeneratlon: biochemical mechanisms and potential roles in Alzheimer's disease and beyond" Chem. Soc. Rev., 2014, 43, 6839.
Grazia D'Onofrio "Advances in the identification of g-secretase inhibitors for the treatment of Alzheimer's disease" Expert Opinion on Drug Discovery 2012, 7, 20-37.
Julie, J.-P. "Transgenic mouse models of amyotrophic lateral sclerosis" Biochimica at Biophysica Acta 1762 (2006) 1013-1024.
Petit-Demouliere et. al. "Forced swimming test in mice: a review of antidepressant activity." Psychopharmacology 2005, 177, 245-255.
Intellihealth, "Schizophrenia", online, accessed Apr. 29, 2008, "http://www.intelihealth.com/IH/ihtIH/WSIHW000/8271/8694/188010.html?d=dmtHealthAZ".
Eric R. Marcotte J "Animal models of schizophrenia: a critical review" Psychiatry Neurosci 2001;26(5):395-410.
Simone, Oncology: Introduction, Cecil Textbook of Medicine, 20th Edition, 1996 vol. 1, pp. 1004-1010.
Howington "Treatment of Stage I and II Non-small Cell Lung Cancer Diagnosis and Management of Lung Cancer, 3rd ed: American College of Chest Physicians Evidence-Based Clinical Practice Guidelines" Chest 2013; 143(5)(Suppl):e278S-e313S.
Socinski "Treatment of Stage IV Non-small Cell Lung Cancer Diagnosis and Management of Lung Cancer, 3rd ed: American College of Chest Physicians Evidence-Based Clinical Practice Guideline" Chest 2013; 143(5)(Suppl):e341S-e368S.
Jett Treatment of Small Cell Lung Cancer Diagnosis and Management of Lung Cancer, 3rd ed: American College of Chest Physicians Evidence-Based Clinical Practice Guidelines Chest 2013; 143(5)(Suppl):e400S-e419S.
Damia "Contemporary pre-clinical development of anticancer agents—What are the optimal preclinical models?" European Journal of Cancer 2009, 45, 2768-2781.
Sharma "Cell line-based platforms to evaluate the therapeutic efficacy of candidate anticancer agents." Nature Reviews Cancer Apr. 2010, vol. 10, 241-253.
Ocana, A. "Preclinical development of molecular targeted agents for cancer" Nat. Rev. Clin. Oncol. 2011, 8, 200-209.
Ledford "US cancer institute overhauls cell lines" Nature Feb. 25, 2016 vol. 530 p. 391.
Johnson, et. al. "Relationships between drug activity in NCI preclinical in vitro and in vivo models and early clinical trials." British Journal of Cancer 2001, 84, 1424-1431.
Reid "Epilepsy, energy deficiency and new therapeutic approaches including diet" Pharmacology & Therapeutics 144 (2014) 192-201.
Le Bars, et. al. "Animal Models of Nociception" Pharmacological Reviews 2001, 53, 597-652.
Costigan "Neuropathic Pain: A Maladaptive Response of the Nervous System to Damage" Annu. Rev. Neurosci. 2009. 32:1-32.
Fabian "A small molecule-kinase interaction map for clinical kinase inhibitors" Nature Biotechnology 2005, 23, 329-336.
Wolff, Manfred E. "Burger's Medicinal Chemistry, 5ed, Part I", John Wiley & Sons, 1995, pp. 975-977.
Banker (Modern Pharmaceutics) Banker, G.S. et al, "Modern Pharmaceutics, 3ed.", Marcel Dekker, New York, 1996, pp. 4 and 596.
G. Furlotti et al., J. Med. Chem., 2015, 58: 8920-8937.
S. Phukan et al., British Journal of Pharmacology, 2010, 160:1-19.
Abstract of Costemale-Lacoste et al., Encephale, 2016, 42(2): 156-64.
Omata et al., Int. J. Neuropsycopharmacology, 2011, 14(2): 711-717.
D. Hanger et al., Neuroscience Letters, 1992, 147: 58-62.
K. Spittaels et al., The Journal of Biological Chemistry, 2000, 275: 41340-41349.
F. Hernandez et al., FEBs Letters, 2008, 582: 3848-3854.
B. Leger et al., Muscle & Nerve, Jul. 2009, 69-78.
D. Galimberti et al., Neuroscience Letters, 2011, 497: 46-48.
R. S. Jope et al., Current Drug Targets, 2006, 7:1421-1434.
T. D. Gould, Expert Opin. Ther. Targets, 2006, 10(3): 377-392.
E. S. Emamian et al., Nature Genetics, 2004, 36(2): 131-137.
J.-M. Beaulieu et al., PNAS, 2004, 101(14): 5099-5104.
H. P. G. Joaquim et al., Schizophrenia Research, 2018, 195: 402-405.
J. Lavoie et al., Biol. Psychiatry, 2014, 76: 93-100.

* cited by examiner

1H-INDAZOLE-3-CARBOXAMIDE COMPOUNDS AS GLYCOGEN SYNTHASE KINASE 3 BETA INHIBITORS

CROSS REFERENCE TO RELATED APPLICATIONS

This application is continuation of U.S. patent application Ser. No. 14/373,100, filed on Jul. 18, 2014, which was a 371 application of International Patent Application No. PCT/EP13/052400, filed on Feb. 7, 2013, and claims priority to European Patent Application No. 12156292.0, filed on Feb. 12, 2012.

FIELD OF THE INVENTION

The present invention relates to 1H-indazole-3-carboxamide compounds acting as glycogen synthase kinase 3 beta (GSK-3β) inhibitors and to their use in the treatment of GSK-3β-related disorders such as (i) insulin-resistance disorders; (ii) neurodegenerative diseases; (iii) mood disorders; (iv) schizophrenic disorders; (v) cancerous disorders; (vi) inflammation, (vii) substance abuse disorders; (viii) epilepsies; and (ix) neuropathic pain.

STATE OF THE ART

Protein kinases constitute a large family of structurally related enzymes, which transfer phosphate groups from high-energy donor molecules (such as adenosine triphosphate, ATP) to specific substrates, usually proteins. After phosphorylation, the substrate undergoes to a functional change, by which kinases can modulate various biological functions.

In general, protein kinases can be divided in several groups, according to the substrate that is phosphorylated. For example, serine/threonine kinase phosphorylates the hydroxyl group on the side chain of serine or threonine aminoacid.

Glycogen synthase kinases 3 (GSK-3) are constitutively active multifunctional enzymes, quite recently discovered, belonging to the serine/threonine kinases group.

Human GSK-3 are encoded by two different and independent genes, which leads to GSK-3α and GSK-3β proteins, with molecular weights of about 51 and 47 kDa, respectively. The two isoforms share nearly identical sequences in their kinase domains, while outside of the kinase domain, their sequences differ substantially (Benedetti et al., *Neuroscience Letters*, 2004, 368, 123-126). GSK-3α is a multifunctional protein serine kinase and GSK-3β is a serine-threonine kinase.

It has been found that GSK-3β is widely expressed in all tissues, with widespread expression in the adult brain, suggesting a fundamental role in neuronal signaling pathways (Grimes and Jope, *Progress in Neurobiology*, 2001, 65, 391-426). Interest in glycogen synthase kinases 3 arises from its role in various physiological pathways, such as, for example, metabolism, cell cycle, gene expression, embryonic development oncogenesis and neuroprotection (Geetha et al., *British Journal Pharmacology*, 2009, 156, 885-898).

GSK-3β was originally identified for its role in the regulation of glycogen synthase for the conversion of glucose to glycogen (Embi et al., *Eur J Biochem*, 1980, 107, 519-527). GSK-3β showed a high degree of specificity for glycogen synthase.

Type 2 diabetes was the first disease condition implicated with GSK-3β, due to its negative regulation of several aspects of insulin signaling pathway. In this pathway 3-phosphoinositide-dependent protein kinase 1 (PDK-1) activates PKB, which in turn inactivates GSK-3β. This inactivation of GSK-3β leads to the dephosphorylation and activation of glycogen synthase, which helps glycogen synthesis (Cohen et al., *FEBS Lett.*, 1997, 410, 3-10). Moreover, selective inhibitors of GSK-3β are expected to enhances insulin signaling in prediabetic insulin-resistant rat skeletal muscle, thus making GSK-3β an attractive target for the treatment of skeletal muscle insulin resistance in the pre-diabetic state (Dokken et al., *Am J. Physiol. Endocrinol. Metab.*, 2005, 288, E1188-E1194).

GSK-3β was also found to be a potential drug target in others pathological conditions due to insulin-resistance disorders, such as syndrome X, obesity and polycystic ovary syndrome (Ring D B et al., *Diabetes*, 2003, 52: 588-595).

It has been found that GSK-3β is involved in the abnormal phosphorylation of pathological tau in Alzheimer's disease (Hanger et al., *Neurosci. Lett.*, 1992, 147, 58-62; Mazanetz and Fischer, *Nat Rev Drug Discov.*, 2007, 6, 464-479; Hong and Lee, *J. Biol. Chem.*, 1997, 272, 19547-19553). Moreover, it was proved that early activation of GSK-3β, induced by apolipoprotein ApoE4 and β-amyloid, could lead to apoptosis and tau hyperphosphorylation (Cedazo-Minguez et al., *Journal of Neurochemistry*, 2003, 87, 1152-1164). Among other aspect of Alzheimer's disease, it was also reported the relevance of activation of GSK-3β at molecular level (Hernandez and Avila, *FEBS Letters*, 2008, 582, 3848-3854).

Moreover, it was demonstrated that GSK-3β is involved in the genesis and maintenance of neurodegenerative changes associated with Parkinson's disease (Duka T. et al., *The FASEB Journal*, 2009; 23, 2820-2830).

Accordingly to these experimental observations, inhibitors of GSK-3β may find applications in the treatment of the neuropathological consequences and the cognitive and attention deficits associated with tauopathies; Alzheimer's disease; Parkinson's disease; Huntington's disease (the involvement of GSK-3β in such deficits and diseases is disclosed in Meijer L. et al., *TRENDS Pharm Sci*, 2004; 25, 471-480); dementia, such as, but not limited to, vascular dementia, post-traumatic dementia, dementia caused by meningitis and the like; acute stroke; traumatic injuries; cerebrovascular accidents; brain and spinal cord trauma; peripheral neuropathies; retinopathies and glaucoma (the involvement of GSK-3β in such conditions is disclosed in WO 2010/109005).

The treatment of spinal neurodegenerative disorders, like amyotrophic lateral sclerosis, multiple sclerosis, spinal muscular atrophy and neurodegeneration due to spinal cord injury has been also suggested in several studies related to GSK-3β inhibition, such as, for example in Calderó J. et al., "Lithium prevents excitotoxic cell death of motoneurons in organotypic slice cultures of spinal cord", Neuroscience. 2010 Feb. 17; 165(4):1353-69, Léger B. et al., "Atrogin-1, MuRF1, and FoXO, as well as phosphorylated GSK-3beta and 4E-BP1 are reduced in skeletal muscle of chronic spinal cord-injured patients", Muscle Nerve, 2009 July; 40(1):69-78, and Galimberti D. et al., "GSK3β genetic variability in patients with Multiple Sclerosis", Neurosci Lett. 2011 Jun. 15; 497(1):46-8. Furthermore, GSK-3β has been linked to the mood disorders, such as bipolar disorders, depression, and schizophrenia.

Inhibition of GSK-3β may be an important therapeutic target of mood stabilizers, and regulation of GSK-3β may be involved in the therapeutic effects of other drugs used in psychiatry. Dysregulated GSK-3β in mood disorder, bipolar disorder, depression and schizophrenia could have multiple effects that could impair neural plasticity, such as modulation of neuronal architecture, neurogenesis, gene expression and the ability of neurons to respond to stressful, potentially lethal conditions (Jope and Roh, *Curr. Drug Targets*, 2006, 7, 1421-1434).

The role of GSK-3β in mood disorder was highlighted by the study of lithium and valproate (Chen et al., *J. Neurochem.*, 1999, 72, 1327-1330; Klein and Melton, *Proc. Natl. Acad. Sci. USA*, 1996, 93, 8455-8459), both of which are GSK-3β inhibitors and are used to treat mood disorders. There are also existing reports from the genetic perspective supporting the role of GSK-3β in the disease physiology of bipolar disorder (Gould, *Expert. Opin. Ther. Targets*, 2006, 10, 377-392).

It was reported a decrease in AKT1 protein levels and its phosphorylation of GSK-3β at Serine-9 in the peripheral lymphocytes and brains of individuals with schizophrenia. Accordingly, this finding supports the proposal that alterations in AKT1-GSK-3β signaling contribute to schizophrenia pathogenesis (Emamian et al., *Nat Genet*, 2004, 36, 131-137).

Additionally, the role of GSK-3β in cancer is a well-accepted phenomenon.

The potential of small molecules that inhibit GSK-3β has been evidenced for some specific cancer treatments (Jia Luo, *Cancer Letters*, 2009, 273, 194-200). GSK-3β expression and activation are associated with prostate cancer progression (Rinnab et al., Neoplasia, 2008, 10, 624-633) and the inhibition of GSK3b was also proposed as specific target for pancreatic cancer (Garcea et al., *Current Cancer Drug Targets*, 2007, 7, 209-215) and ovarian cancer (Qi Cao et al., Cell Research, 2006, 16 671-677). Acute inhibition of GSK-3β in colon-rectal cancer cells activates p53-dependent apoptosis and antagonizes tumor growth (Ghosh et al., Clin Cancer Res 2005, 11, 4580-4588).

The identification of a functional role for GSK-3β in MLL-associated leukaemia suggests that GSK-3β inhibition may be a promising therapy that is selective for transformed cells that are dependent on HOX overexpression (Birch et al., Cancer Cell, 2010, 17, 529-531).

GSK-3β is involved in numerous inflammatory signalling pathways, for example, among others GSK-3β inhibition has been shown to induce secretion of the anti-inflammatory cytokine IL-10. According to this finding, GSK-3β inhibitors could be useful to regulate suppression of inflammation (G. Klamer et al., *Current Medicinal Chemistry*, 2010, 17(26), 2873-2281, Wang et al., Cytokine, 2010, 53, 130-140).

GSK-3β inhibition has been also shown to attenuate cocaine-induced behaviors in mice. The administration of cocaine in mice pretreated with a GSK-3β inhibitor demonstrated that pharmacological inhibition of GSK3 reduced both the acute behavioral responses to cocaine and the long-term neuroadaptations produced by repeated cocaine (*Cocaine-induced hyperactivity and sensitization are dependent on GSK3*, Miller J S et al. *Neuropharmacology.* 2009 June; 56(8):1116-23, Epub 2009 Mar. 27).

The role of GSK-3β in the development of several forms of epilepsies has been demonstrated in several studies, which suggest that inhibition of GSK-3J3 could be a pathway for the treatment of epilepsy (*Novel glycogen synthase kinase 3 and ubiquitination pathways in progressive myoclonus epilepsy*, Lohi H et al., *Hum Mol Genet.* 2005 Sep. 15; 14(18):2727-36 *and Hyperphosphorylation and aggregation of Tau in laforin-deficient mice, an animal model for Lafora disease*, Puri R et al., *J Biol Chem.* 2009 Aug. 21; 284(34):22657-63).

The relationship between GSK-3β inhibition and treatment of neuropathic pain has been demonstrated in Mazzardo-Martins L. et al., "Glycogen synthase kinase 3-specific inhibitor AR-A014418 decreases neuropathic pain in mice: evidence for the mechanisms of action", Neuroscience. 2012 Dec. 13; 226, and Xiaoping Gu et al., "The Role of Akt/GSK3β Signaling Pathway in Neuropathic Pain in Mice", Poster A525, *Anesthesiology* 2012 Oct. 13-17, 2012 Washington.

A review on GSK-3β, its function, its therapeutic potential and its possible inhibitors is given in "GSK-3β: role in therapeutic landscape and development of modulators" (S. Phukan et al., *British Journal of* Pharmacology (2010), 160, 1-19).

WO 2004/014864 discloses 1H-indazole-3-carboxamide compounds as selective cyclin-dependant kinases (CDK) inhibitors. Such compounds are assumed to be useful in the treatment of cancer, through a mechanism mediated by $CDK_2$, and neurodegenerative diseases, in particular Alzheimer's disease, through a mechanism mediated by $CDK_5$, and as anti-viral and anti-fungine, through a mechanism mediated by $CDK_7$, $CDK_8$ and $CDK_9$.

Cyclin-dependant kinases (CDKs) are serine/threonine kinases, first discovered for their role in regulating the cell cycle. CDKs are also involved in regulating transcription, mRNA processing, and the differentiation of nerve cells. Such kinases activate only after their interaction and binding with regulatory subunits, namely cyclins.

Moreover, 1H-indazole-3-carboxamide compounds were also described as analgesics in the treatment of chronic and neuropathic pain (see, for example, WO 2004/074275 and WO 2004/101548) and as $5-HT_4$ receptor antagonists, useful in the treatment of gastrointestinal disorders, central nervous system disorders and cardiovascular disorders (see, for example, WO 1994/10174).

SUMMARY OF THE INVENTION

As GSK-3β had been only recently discovered as a pharmacological target, there is a strong need to find compounds that selectively inhibits GSK-3β.

The Applicant has surprisingly found new 1H-indazole-3-carboxamide compounds according to the following formula (I).

The Applicant has also surprisingly found that said new compounds are capable of inhibiting GSK-3β and have very high affinity for GSK-3β, when compared with other kinases. Thus, said compounds are capable of selectively inhibiting GSK-3β.

Accordingly, the compounds according to this invention are useful for the treatment of the pathological conditions arising from the uncontrolled activation and/or over-expression of GSK-3β, selected from the group comprising (i) insulin-resistance disorders, such as type-2 diabetes, syndrome X, obesity and polycystic ovary syndrome; (ii) neurodegenerative diseases, such as Parkinson's disease, Alzheimer's disease, Huntington's disease and spinal neurodegenerative disorders; (iii) mood disorders, such as bipolar disorders and depressive disorders; (iv) schizophrenic disorders; (v) cancerous disorders, such as prostate, pancreatic, ovarian, and colon-rectal cancer and MLL-associated leukaemia; (vi) inflammation; (vii) substance abuse disorders; (viii) epilepsies; and (ix) neuropathic pain.

Then, in a first aspect, the present invention relates to 1H-indazole-3-carboxamide compounds having the following general formula (I):

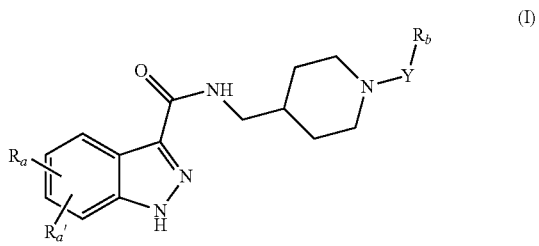

wherein $R_a$ and $R_a'$, equal or different each other, is a hydrogen atom; a halogen atom; a hydroxy group; a $C_1$-$C_6$ alkyl, $C_2$-$C_6$ alkenyl, $C_2$-$C_6$ alkynyl and $C_1$-$C_6$ alkoxy group, optionally substituted by one or more substituents selected from the group consisting of halogen, hydroxy, —$NH_2$, and $C_1$-$C_3$ alkoxy; a carbocyclic or heterocyclic ring, aliphatic or aromatic, having from 3 to 12 members, optionally substituted by one or more substituents selected from the group consisting of halogen, hydroxy, $C_1$-$C_6$ alkyl, $C_1$-$C_6$ alkoxy, —$NR_1R_2$, —C(O)OH, —C(O)$OR_1$ and —C(O)$NR_1R_2$;

Y is a bond, a $C_1$-$C_6$ alkyl, $C_2$-$C_6$ alkenyl or $C_2$-$C_6$ alkynyl group, optionally substituted by one or more substituents selected from the group consisting of halogen, hydroxy, —$NH_2$, and $C_1$-$C_3$ alkoxy;

$R_b$ is a $C_1$-$C_6$ alkoxy group; —C(O)OH; —C(O)$OR_1$; —$NO_2$; —NHC(O)$R_1$;

$R_1$ and $R_2$ are independently a hydrogen atom, a $C_1$-$C_4$ alkyl group, a $C_2$-$C_4$ alkenyl group, a $C_2$-$C_4$ alkynyl group, and a phenyl group;

and its salts of addition with pharmaceutically acceptable organic and inorganic acids and bases.

In a second aspect, the present invention relates to the use of 1H-indazole-3-carboxamide compounds having the following general formula (I)

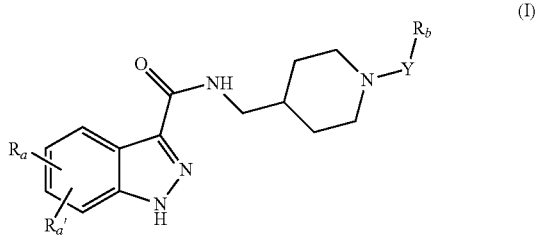

wherein $R_a$ and $R_a'$, equal or different each other, is a hydrogen atom; a halogen atom; a hydroxy group; a $C_1$-$C_6$ alkyl, $C_2$-$C_6$ alkenyl, $C_2$-$C_6$ alkynyl and $C_1$-$C_6$ alkoxy group, optionally substituted by one or more substituents selected from the group consisting of halogen, hydroxy, —$NH_2$, and $C_1$-$C_3$ alkoxy; a carbocyclic or heterocyclic ring, aliphatic or aromatic, having from 3 to 12 members, optionally substituted by one or more substituents selected from the group consisting of halogen, hydroxy, $C_1$-$C_6$ alkyl, $C_1$-$C_6$ alkoxy, —$NR_1R_2$, —C(O)OH, —C(O)$OR_1$ and —C(O)$NR_1R_2$;

Y is a bond, a $C_1$-$C_6$ alkyl, $C_2$-$C_6$ alkenyl or $C_2$-$C_6$ alkynyl group, optionally substituted by one or more substituents selected from the group consisting of halogen, hydroxy, —$NH_2$, and $C_1$-$C_3$ alkoxy;

$R_b$ is a $C_1$-$C_6$ alkoxy group; —C(O)OH; —C(O)$OR_1$; —$NO_2$; —NHC(O)$R_1$;

$R_1$ and $R_2$ are independently a hydrogen atom, a $C_1$-$C_4$ alkyl group, a $C_2$-$C_4$ alkenyl group, a $C_2$-$C_4$ alkynyl group, and a phenyl group;

and its salts of addition with pharmaceutically acceptable organic and inorganic acids and bases;

for the treatment of a disease arising from the uncontrolled activation and/or over-expression of GSK-3β, selected from the group consisting of (i) insulin-resistance disorders, such as type-2 diabetes, syndrome X, obesity and polycystic ovary syndrome; (ii) neurodegenerative diseases, such as Parkinson's disease, Alzheimer's disease, Huntington's disease and spinal neurodegenerative disorders; (iii) mood disorders, such as bipolar disorders and depressive disorders; (iv) schizophrenic disorders; (v) cancerous disorders, such as prostate, pancreatic, ovarian, and colon-rectal cancer and MLL-associated leukaemia; (vi) inflammation; (vii) substance abuse disorders; (viii) epilepsies; and (ix) neuropathic pain.

In a further aspect, the present invention relates to a method of treatment of a pathological state arising from the uncontrolled activation and/or over-expression of GSK-3β, selected from the group consisting of (i) insulin-resistance disorders, such as type-2 diabetes, syndrome X, obesity and polycystic ovary syndrome; (ii) neurodegenerative diseases, such as Parkinson's disease, Alzheimer's disease, Huntington's disease and spinal neurodegenerative disorders; (iii) mood disorders, such as bipolar disorders and depressive disorders; (iv) schizophrenic disorders; (v) cancerous disorders, such as prostate, pancreatic, ovarian, and colon-rectal cancer and MLL-associated leukaemia; (vi) inflammation; (vii) substance abuse disorders; (viii) epilepsies; and (ix) neuropathic pain by the administration to a human being in need thereof of an effective amount of a 1H-indazole-3-carboxamide having the following general formula (I)

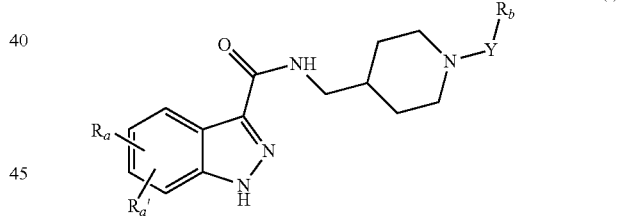

wherein $R_a$ and $R_a'$, equal or different each other, is a hydrogen atom; a halogen atom; a hydroxy group; a $C_1$-$C_6$ alkyl, $C_2$-$C_6$ alkenyl, $C_2$-$C_6$ alkynyl and $C_1$-$C_6$ alkoxy group, optionally substituted by one or more substituents selected from the group consisting of halogen, hydroxy, —$NH_2$, and $C_1$-$C_3$ alkoxy; a carbocyclic or heterocyclic ring, aliphatic or aromatic, having from 3 to 12 members, optionally substituted by one or more substituents selected from the group consisting of halogen, hydroxy, $C_1$-$C_6$ alkyl, $C_1$-$C_6$ alkoxy, —$NR_1R_2$, —C(O)OH, —C(O)$OR_1$ and —C(O)$NR_1R_2$;

Y is a bond, a $C_1$-$C_6$ alkyl, $C_2$-$C_6$ alkenyl or $C_2$-$C_6$ alkynyl group, optionally substituted by one or more substituents selected from the group consisting of halogen, hydroxy, —$NH_2$, and $C_1$-$C_3$ alkoxy;

$R_b$ is a $C_1$-$C_6$ alkoxy group; —C(O)OH; —C(O)$OR_1$; —$NO_2$; —NHC(O)$R_1$;

$R_1$ and $R_2$ are independently a hydrogen atom, a $C_1$-$C_4$ alkyl group, a $C_2$-$C_4$ alkenyl group, a $C_2$-$C_4$ alkynyl group, and a phenyl group;

and its salts of addition with pharmaceutically acceptable organic and inorganic acids and bases.

The present invention also includes the prodrugs, stereoisomers, and enantiomers of the compounds of formula (I) described above.

DETAILED DESCRIPTION OF THE INVENTION

Throughout the present description and the following claims, "$C_{1-6}$ alkyl" is intended to indicate linear or branched alkyl groups having from 1 to 6 carbon atoms, such as methyl, ethyl, propyl, isopropyl, n-butyl, isobutyl, sec-butyl, tert-butyl, n-pentyl, sec-pentyl, 3-pentyl, iso-pentyl, neo-pentyl, n-hexyl, sec-hexyl and neo-hexyl.

Throughout the present description and the following claims, "$C_{1-4}$ alkyl" is intended to indicate linear or branched alkyl groups having from 1 to 4 carbon atoms, such as methyl, ethyl, propyl, isopropyl, n-butyl, isobutyl, sec-butyl and tert-butyl.

Throughout the present description and the following claims, "$C_{1-3}$ alkyl" is intended to indicate linear or branched alkyl groups having from 1 to 3 carbon atoms, such as methyl, ethyl, propyl and isopropyl.

Throughout the present description and the following claims, "$C_{2-6}$ alkenyl" is intended to indicate linear or branched alkyl groups having from 2 to 6 carbon atoms and at least one double bond, such as ethenyl (vinyl), 1-propenyl, 2-propenyl (allyl), isopropenyl, butenyl, pentenyl and hexenyl.

Throughout the present description and the following claims, "$C_{2-4}$ alkenyl" is intended to indicate linear or branched alkyl groups having from 2 to 4 carbon atoms and at least one double bond, such as ethenyl (vinyl), 1-propenyl, 2-propenyl (allyl), isopropenyl and butenyl.

Throughout the present description and the following claims, "$C_{2-6}$ alkynyl" is intended to indicate linear or branched alkyl groups having from 2 to 6 carbon atoms and at least one triple bond, such as ethynyl, 1-propynyl, 2-propynyl (propargyl), butynyl, pentynyl and hexynyl.

Throughout the present description and the following claims, "$C_{2-4}$ alkynyl" is intended to indicate linear or branched alkyl groups having from 2 to 4 carbon atoms and at least one triple bond, such as ethynyl, 1-propynyl, 2-propynyl (propargyl) and butynyl.

Throughout the present description and the following claims, "$C_{1-6}$ alkoxy" is intended to indicate linear or branched alkoxy groups having from 1 to 6 carbon atoms, such as methoxy, ethoxy, n-propoxy, iso-propoxy, n-butoxy, tert-butoxy, n-penthoxy, sec-penthoxy, isopenthoxy and n-esiloxy.

Throughout the present description and the following claims, "$C_{1-3}$ alkoxy" is intended to indicate linear or branched alkoxy groups having from 1 to 3 carbon atoms, such as methoxy, ethoxy, n-propoxy and iso-propoxy.

According to a preferred embodiment of the invention, the meanings of $R_a$, $R_a'$, $R_b$ and Y of the formula (I) above are described here in below.

Preferably, $R_a$ and $R_a'$, equal or different each other, is a hydrogen atom; a halogen atom, selected from chlorine, bromine and iodine; a hydroxy group; a $C_1$-$C_6$ alkyl, and $C_1$-$C_6$ alkoxy group, optionally substituted by one or more substituents selected from the group consisting of halogen, hydroxy, —$NH_2$, or $C_1$-$C_3$ alkoxy; a carbocyclic or heterocyclic ring, aliphatic or aromatic, having from 4 to 10 members, optionally substituted by one or more substituents selected from the group consisting of halogen, hydroxy, $C_1$-$C_6$ alkyl, $C_1$-$C_6$ alkoxy, —$NR_1R_2$, —C(O)OH, —C(O)OR$_1$ and —C(O)NR$_1$R$_2$.

More preferably, $R_a$ and $R_a'$, equal or different each other, is a halogen atom, selected from chlorine and bromine; a hydroxy group; a $C_1$-$C_6$ alkyl group; a $C_1$-$C_6$ alkoxy group; or a carbocyclic or heterocyclic ring, aliphatic or aromatic, having from 5 to 6 members, optionally substituted by one or more substituents, selected from the group consisting of halogen, hydroxy, $C_1$-$C_6$ alkyl, $C_1$-$C_6$ alkoxy, —$NR_1R_2$ and —C(O)OH.

Advantageously, said carbocyclic or heterocyclic ring, aliphatic or aromatic, having 5 or 6 members is selected from phenyl, pyridine, pyrimidine, pyrazine, pyridazine, pyrrole, furan, thiophene, oxazole, isoxazole, thiazole, isothiazole, 2H-pyran, cyclohexyl, cyclopenthyl piperidine, piperazine.

Even more preferably, $R_a$ and $R_a'$, equal or different each other, is a bromine atom, a hydroxy group; a $C_1$-$C_3$ alkoxy group; or an aromatic carbocyclic or heterocyclic ring, having 6 members, optionally substituted by one or two substituents selected from the group consisting of halogen, hydroxy, $C_1$-$C_3$ alkyl, $C_1$-$C_3$ alkoxy, —$NR_1R_2$ and —C(O)OH.

In a preferred embodiment, said carbocyclic or heterocyclic ring, aliphatic or aromatic, having 6 members is selected from phenyl, pyridine, pyrimidine, pyrazine, pyridazine, 2H-pyran, cyclohexyl, piperidine, piperazine.

In an even more preferred embodiment, said carbocyclic or heterocyclic ring, aliphatic or aromatic, having 6 members is selected from phenyl, pyridine, pyrimidine, 2H-pyran, cyclohexyl.

In an even more preferred embodiment, said carbocyclic or heterocyclic ring, aliphatic or aromatic, having 5 members is selected from oxazole and isoxazole.

Preferably, Y is a bond, $C_1$-$C_6$ alkyl group, optionally substituted by one or more substituents selected from the group consisting of halogen, hydroxy, —$NH_2$, and $C_1$-$C_3$ alkoxy.

More preferably, Y is a $C_1$-$C_6$ alkyl group.

Even more preferably, Y is a $C_1$-$C_3$ alkyl group.

Preferably, $R_b$ is a $C_1$-$C_6$ alkoxy group; —C(O)OH; —C(O)OR$_1$ or —NHCOR$_1$.

More preferably, $R_b$ is a $C_1$-$C_6$ alkoxy group or —C(O)OH.

Even more preferably, $R_b$ is a $C_1$-$C_3$ alkoxy group or —C(O)OH. Preferably, $R_1$ and $R_2$ are independently a hydrogen atom, a $C_1$-$C_4$ alkyl group, or a phenyl group.

More preferably, $R_1$ and $R_2$ are independently a $C_1$-$C_3$ alkyl group.

Even more preferably, $R_1$ and $R_2$ are both a methyl group.

The compounds according to the present invention are preferably employed as salts with pharmaceutically acceptable organic and inorganic acids or bases.

Preferably, the pharmaceutically acceptable organic acids are selected from the group consisting of oxalic, maleic, methanesulphonic, paratoluenesulphonic, succinic, citric, malic, tartaric and lactic acid.

Preferably, the pharmaceutically acceptable organic bases are selected from the group consisting of tromethamine, lysine, arginine, glycine, alanine and ethanolamine.

Preferably, the pharmaceutically acceptable inorganic acids are selected from the group consisting of hydrochloric, hydrobromic, phosphoric and sulphuric acid.

Preferably, the pharmaceutically acceptable inorganic bases are selected from the group consisting of hydroxide or carbonate of alkaline or alkaline-earth metals, such as sodium, potassium and calcium.

The present invention also includes the prodrugs, stereoisomers, and enantiomers of the compounds of formula (I) described above.

As used herein the term "prodrug" refers to an agent, which is converted into the parent drug in vivo by some physiological chemical process (e.g., a prodrug on being brought to the physiological pH is converted to the desired drug form). Prodrugs are often useful because, in some situations, they may be easier to administer than the parent drug. They may, for instance, be bioavailable by oral administration whereas the parent drug is not. The prodrug may also have improved solubility in pharmacological compositions over the parent drug. An example, without limitation, of a prodrug would be a compound of the present invention wherein it is administered as an ester (the "prodrug") to facilitate transmittal across a cell membrane where water solubility is not beneficial, but then it is metabolically hydrolyzed to the carboxylic acid once inside the cell where water solubility is beneficial.

Prodrugs have many useful properties. For example, a prodrug may be more water-soluble than the ultimate drug, thereby facilitating intravenous administration of the drug. A prodrug may also have a higher level of oral bioavailability than the ultimate drug. After administration, the prodrug is enzymatically or chemically cleaved to deliver the ultimate drug in the blood or tissue.

Ester prodrugs of the compounds disclosed herein are specifically contemplated. An ester may be formed from a carboxylic acid functional group linked to a compound of formula (I) above by reaction with an alcohol or phenol. Alternatively, an ester may be formed from a hydroxyl functional group linked to a compound of formula (I) above by reaction with a carboxylic acid or an amino acid. While not intending to be limiting, an ester may be an alkyl ester, an aryl ester, or a heteroaryl ester. The term alkyl has the meaning generally understood by those skilled in the art and refers to linear, branched, or cyclic alkyl moieties. $C_{1-6}$alkyl esters are particularly useful, where alkyl part of the ester has from 1 to 6 carbon atoms and includes, but is not limited to, methyl, ethyl, propyl, isopropyl, n-butyl, sec-butyl, iso-butyl, t-butyl, pentyl isomers, hexyl isomers, cyclopropyl, cyclobutyl, cyclopentyl, cyclohexyl, and combinations thereof having from 1-6 carbon atoms.

The compounds of the present invention according to formula (I) above can be used for the treatment of a pathological state arising from the uncontrolled activation and/or overexpression of GSK-3β, selected from the group consisting of (i) insulin-resistance disorders; (ii) neurodegenerative diseases; (iii) mood disorders; (iv) schizophrenic disorders; (v) cancerous disorders; (vi) inflammation; (vii) substance abuse disorders; (viii) epilepsies; and (ix) neuropathic pain.

Advantageously, insulin-resistance disorders are type-2 diabetes, syndrome X, obesity and polycystic ovary syndrome.

Advantageously, acute and chronic neurodegenerative diseases are Parkinson's disease, Alzheimer's disease, Huntington's disease and spinal neurodegenerative disorders.

Preferably, spinal neurodegenerative disorders are amyotrophic lateral sclerosis, multiple sclerosis, spinal muscular atrophy and neurodegeneration due to spinal cord injury.

Advantageously, mood disorders are bipolar disorders and depressive disorders.

Preferably, bipolar disorders are bipolar I, bipolar II, cyclothymia and bipolar disorder not otherwise specified (BD-NOS), Preferably, depressive disorders are major depressive disorder (MDD), atypical depression (AD), melancholic depression, psychotic major depression (PMD), catatonic depression, postpartum depression (PPD), seasonal affective disorder (SAD), dysthymia, and depressive disorder not otherwise specified (DD-NOS)

Advantageously, schizophrenic disorders are paranoid schizophrenia, disorganized schizophrenia, catatonic schizophrenia, simple schizophrenia, residual schizophrenia, and undifferentiated schizophrenia.

Advantageously, cancerous disorders are prostate, pancreatic, ovarian, and colon-rectal cancer and MLL-associated leukaemia.

Advantageously, substance abuse disorders are abuse disorders due to psychostimulants.

Typically, the 1H-indazole-3-carboxamide compounds according to formula (I) useful in this invention are administered in the form of a pharmaceutical composition.

Accordingly, a further aspect of the present invention relates to a pharmaceutical composition comprising at least one compound of formula (I) as described above and at least one inert pharmaceutically acceptable excipient.

Preferably, the pharmaceutical composition of the present invention is prepared in suitable dosage forms comprising an effective amount of at least one compound of formula (I) as described above, a salt thereof with a pharmaceutically acceptable organic or inorganic acid or base, or a prodrug thereof, and at least one inert pharmaceutically acceptable excipient.

Examples of suitable dosage forms are tablets, capsules, coated tablets, granules, solutions and syrups for oral administration; solutions, pomade and ointment for topical administration; medicated patches for transdermal administration; suppositories for rectal administration and injectable sterile solutions.

Other suitable dosage forms are those with sustained release and those based on liposomes for oral, injectable or transdermal administration.

The dosage forms can also contain other traditional ingredients such as: preservatives, stabilizers, surfactants, buffers, salts for regulating osmotic pressure, emulsifiers, sweeteners, colorants, flavourings and the like.

The amount of the 1H-indazole-3-carboxamide according to formula (I) or of the pharmaceutically acceptable salt of acid addition thereof in the pharmaceutical composition of the present invention can vary over a wide range depending on known factors, for example, the type of pathology, the severity of the disease, the patient's body weight, the dosage form, the chosen route of administration, the number of administrations per day and the efficacy of the selected 1H-indazole-3-carboxamide compound according to formula (I). However, a person skilled in the art can determine the optimum amount in easily and routinely manner.

Typically, the amount of compound of formula (I) or of the pharmaceutically acceptable salt of acid addition thereof in the pharmaceutical composition of the present invention will be such as to ensure a level of administration from 0.0001 to 100 mg/kg/day. Preferably, the level of administration is from 0.001 to 50 mg/kg/day, and even more preferably from 0.01 to 10 mg/kg/day.

The dosage forms of the pharmaceutical composition of the present invention can be prepared by techniques that are familiar to a pharmaceutical chemist, and comprise mixing, granulation, compression, dissolution, sterilization and the like.

Non-limiting examples of compounds of formula (I) according to the present invention are those of the following table 1.

TABLE 1

| | IUPAC name | Structure |
|---|---|---|
| 1 | [4-({[(5-methoxy-1H-indazol-3-yl)-carbonyl]amino}methyl)piperidin-1-yl]acetic acid | 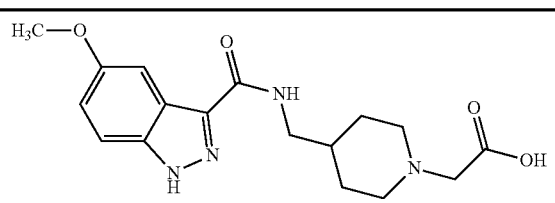 |
| 2 | 5-methoxy-N-{[1-(2-methoxyethyl)-piperidin-4-yl]methyl}-1H-indazole-3-carboxamide | 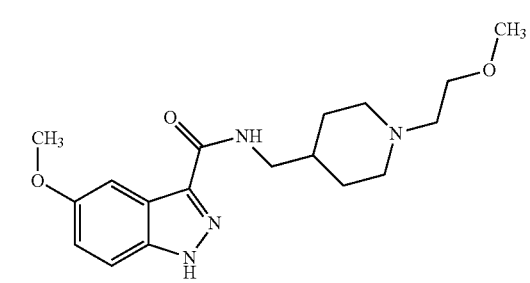 [SMILES: COCCN1CCC(CNC(=O)c2n[nH]c3ccc(OC)cc23)CC1] |
| 3 | [4-({[(5-methoxy-1H-indazol-3-yl)-carbonyl]amino}methyl)piperidin-1-yl]propionic acid | 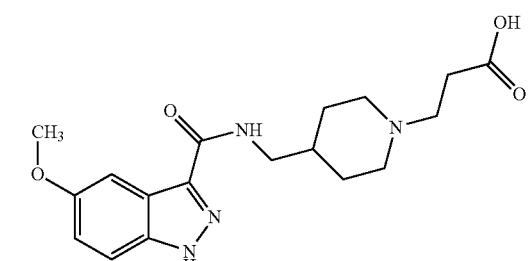 |
| 4 | N-{[1-(2-methoxyethyl)piperidin-4-yl]methyl}-5-(pyridin-3-yl)-1H-indazole-3-carboxamide | 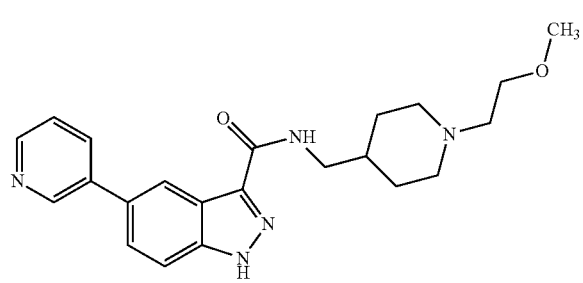 [SMILES: COCCN1CCC(CNC(=O)c2n[nH]c3ccc(-c4cccnc4)cc23)CC1] |
| 5 | N-{[1-(2-methoxyethyl)piperidin-4-yl]methyl}-5-(4-methoxypyridin-3-yl)-1H-indazole-3-carboxamide | 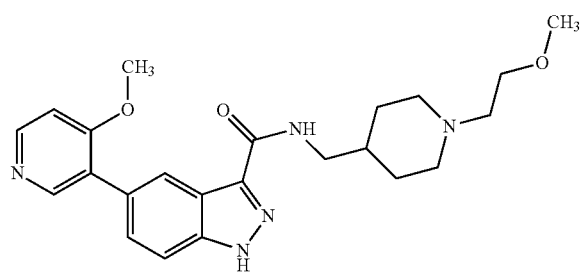 [SMILES: COCCN1CCC(CNC(=O)c2n[nH]c3ccc(-c4cnccc4OC)cc23)CC1] |
| 6 | 5-(2-fluorophenyl)-N-{[1-(2-methoxyethyl)piperidin-4-yl]methyl}-1H-indazole-3-carboxamide | 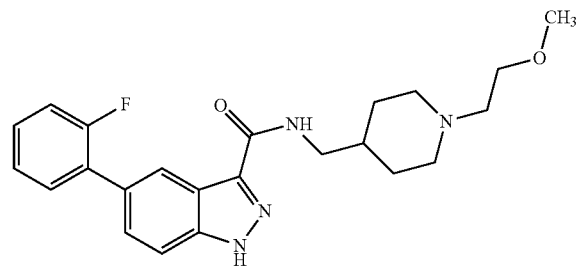 [SMILES: COCCN1CCC(CNC(=O)c2n[nH]c3ccc(-c4ccccc4F)cc23)CC1] |

TABLE 1-continued

| | IUPAC name | Structure |
|---|---|---|
| 7 | N-{[1-(2-methoxyethyl)piperidin-4-yl]methyl}-5-(6-methylpyridin-3-yl)-1H-indazole-3-carboxamide | 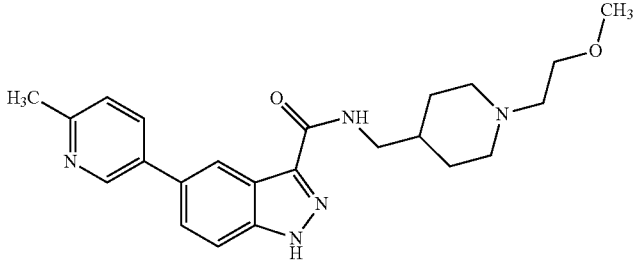 |
| 8 | 5-(2,3-difluorophenyl)-N-{[1-(2-methoxyethyl)piperidin-4-yl]methyl}-1H-indazole-3-carboxamide | 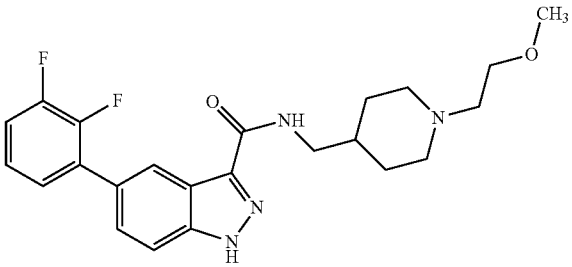 |
| 9 | N-{[1-(2-methoxyethyl)piperidin-4-yl]methyl}-5-phenyl-1H-indazole-3-carboxamide | 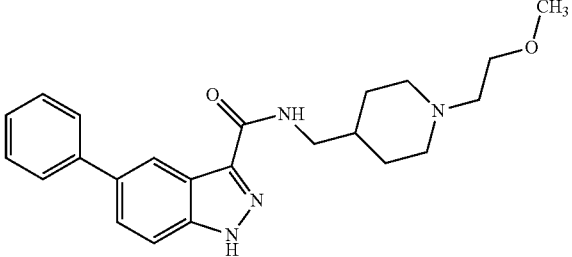 [SMILES: COCCN1CCC(CNC(=O)c2n[nH]c3ccc(-c4ccccc4)cc23)CC1] |
| 10 | N-{[1-(2-methoxyethyl)piperidin-4-yl]methyl}-5-(5-methylpyridin-3-yl)-1H-indazole-3-carboxamide | 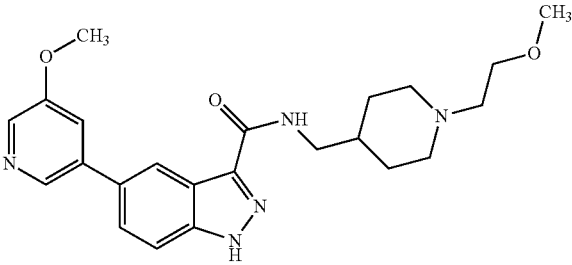 [SMILES: COCCN1CCC(CNC(=O)c2n[nH]c3ccc(-c4cncc(OC)c4)cc23)CC1] |
| 11 | 5-(4-hydroxyphenyl)-N-{[1-(2-methoxyethyl)piperidin-4-yl]methyl}-1H-indazole-3-carboxamide | 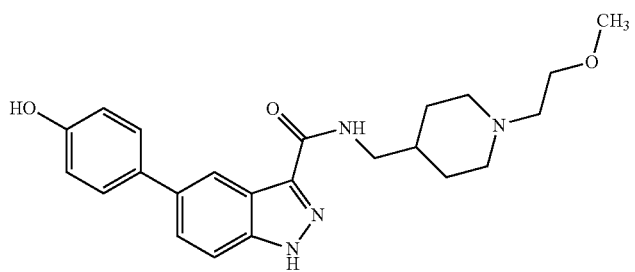 [SMILES: COCCN1CCC(CNC(=O)c2n[nH]c3ccc(-c4ccc(O)cc4)cc23)CC1] |

TABLE 1-continued

| | IUPAC name | Structure |
|---|---|---|
| 12 | N-{[1-(2-methoxyethyl)piperidin-4-yl]methyl}-5-(4-methoxyphenyl)-1H-indazole-3-carboxamide | 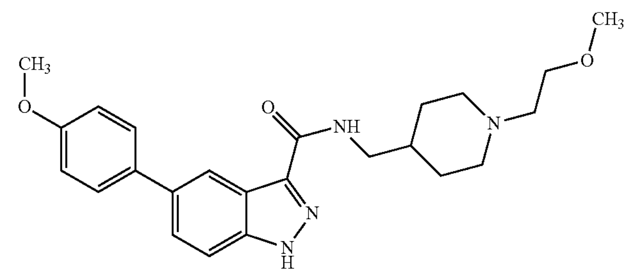 [SMILES: COCCN1CCC(CNC(=O)c2n[nH]c3ccc(-c4ccc(OC)cc4)cc23)CC1] |
| 13 | N-{[1-(2-methoxyethyl)piperidin-4-yl]methyl}-5-(4-methylphenyl)-1H-indazole-3-carboxamide | 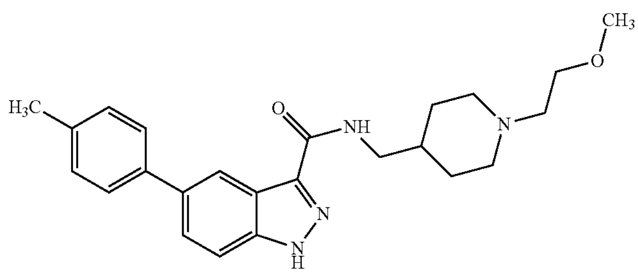 |
| 14 | N-{[1-(2-methoxyethyl)piperidin-4-yl]methyl}-5-(2-methoxypyridin-3-yl)-1H-indazole-3-carboxamide | 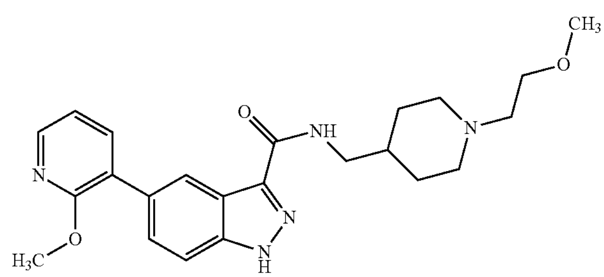 [SMILES: COCCN1CCC(CNC(=O)c2n[nH]c3ccc(-c4cccnc4OC)cc23)CC1] |
| 15 | N-{[1-(2-methoxyethyl)piperidin-4-yl]methyl}-5-(6-methoxypyridin-3-yl)-1H-indazole-3-carboxamide | 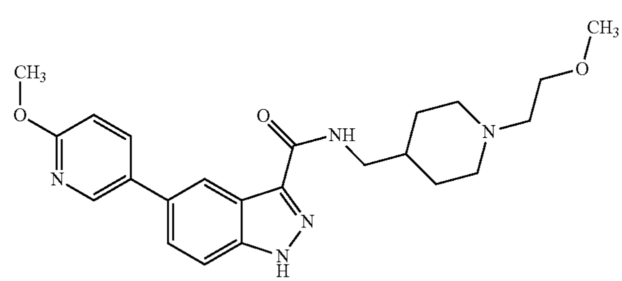 [SMILES: COCCN1CCC(CNC(=O)c2n[nH]c3ccc(-c4ccc(OC)nc4)cc23)CC1] |
| 16 | N-{[1-(2-methoxyethyl)piperidin-4-yl]methyl}-5-(2-methylphenyl)-1H-indazole-3-carboxamide | 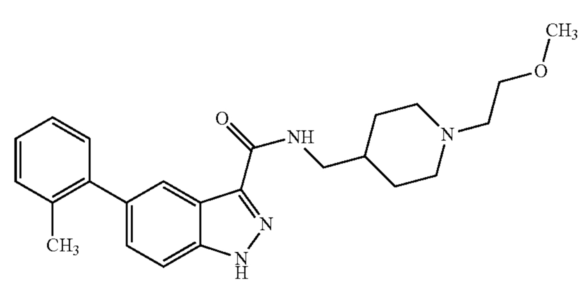 [SMILES: COCCN1CCC(CNC(=O)c2n[nH]c3ccc(-c4ccccc4C)cc23)CC1] |

TABLE 1-continued

| | IUPAC name | Structure |
|---|---|---|
| 17 | 4-[3-({[1-(2-methoxyethyl)piperidin-4-yl]methyl}carbamoyl)-1H-indazol-5-yl]benzoic acid | 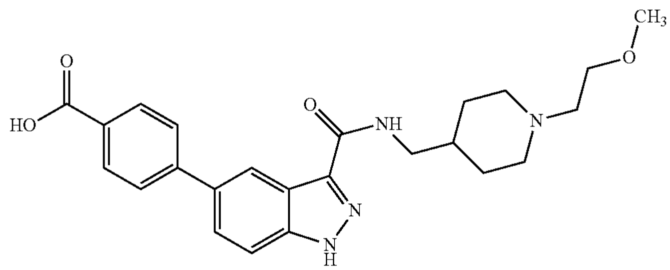 [SMILES: COCCN1CCC(CNC(=O)c2n[nH]c3ccc(-c4ccc(C(=O)O)cc4)cc23)CC1] |
| 18 | 5-(2-ethoxy-4,5-difluorophenyl)-N-{[1-(2-methoxyethyl)piperidin-4-yl]methyl}-1H-indazole-3-carboxamide | 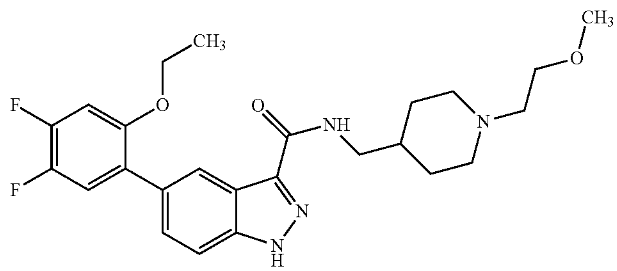 [SMILES: CCOc1cc(F)c(F)cc1-c1ccc2[nH]nc(C(=O)NCC3CCN(CCOC)CC3)c2c1] |
| 19 | 5-bromo-N-{[1-(2-methoxyethyl)piperidine-4-yl]methyl}-1H-indazole-3-carboxamide | 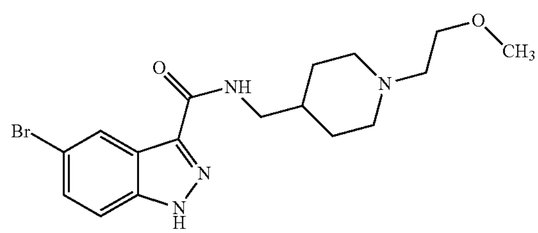 [SMILES: COCCN1CCC(CNC(=O)c2n[nH]c3ccc(Br)cc23)CC1] |

EXPERIMENTAL PART $^1$H-NMR spectroscopy: internal standard=Tetramethylsilane; DMSO-d$_6$=deuterated dimethyl sulfoxide; (s)=singlet; (d)=doublet; (t)=triplet; (br)=broad; (dd)=double doublet; (dt)=double triplet; (ddd)=double double doublet; (dtd)=double triple doublet; (m)=multiplet; J=coupling constant; δ=chemical shift (in ppm).

Preparation of Compounds of Formula (I)

Compounds of formula (I) can be obtained by methods known to persons skilled in the art, for example by the following methods A to D.

Method A

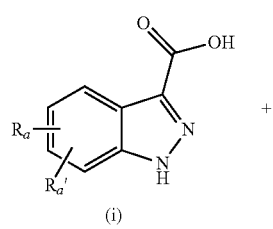

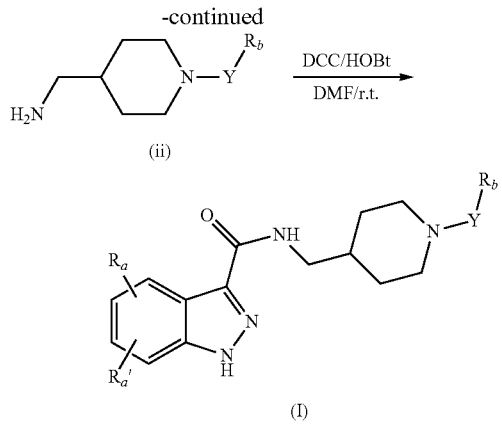

1-Hydroxybenzotriazole (HOBt, 7.40 g, 54.8 mmoles) and N,N'-dicyclohexylcarbodiimide (DCC, 11 g, 53.3 mmoles) were added to a solution of a convenient substituted 1H-indazole-3-carboxylic acid (compound i, 12 g, 49.8 mmoles) in DMF (200 ml) at 0° C. After 1 hour, a solution of a convenient 1-substituted [piperidin-4-yl]methanamine (compound ii, 10 g, 58.1 mmoles) in DMF (100 ml) was added at the same temperature. The mixture was stirred at 0° C. for 2 hours then it was left to reach room temperature during the night. The mixture was diluted with AcOEt then the solid was removed by filtration. The solution was extracted three times with hydrochloridric acid (HCl) 2N. The pH of the acid phase was increased (about 13) with 5N NaOH and solution was extracted three times with dichloromethane (DCM). The organic phase was dried with anhydrous Na$_2$SO$_4$.

The solvent was filtered, evaporated under reduced pressure and the residue was adequately purified.

For example, compound (19) can be prepared according to method A as described below.

Compound (19)

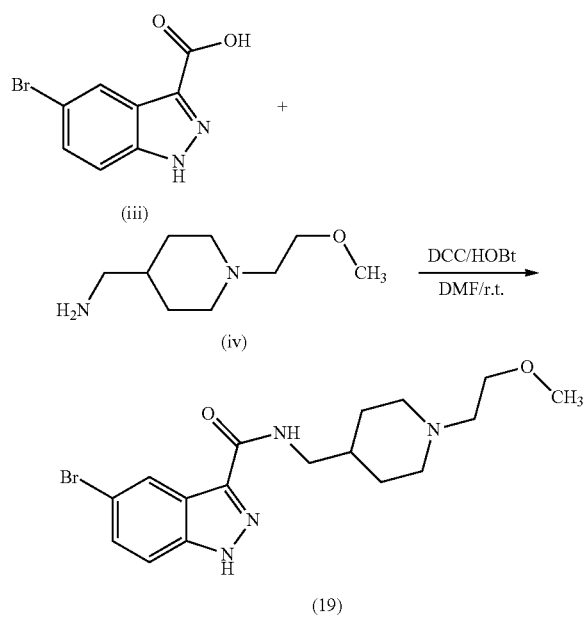

1-Hydroxybenzotriazole (HOBt, 7.40 g, 54.8 mmoles) and N,N'-dicyclohexylcarbodiimide (DCC, 11 g, 53.3 mmoles) were added to a solution of 5-bromo-1H-indazole-3-carboxylic acid (compound iii, 12 g, 49.8 mmoles) in DMF (200 ml) at 0° C. After 1 hour, a solution of 1-[1-(2-methoxyethyl)piperidin-4-yl]methanamine (compound iv, 10 g, 58.1 mmoles) in DMF (100 ml) was added at the same temperature. The mixture was stirred at 0° C. for 2 hours then it was left to reach room temperature during the night. The mixture was diluted with AcOEt then the solid was removed by filtration. The solution was extracted three times with 2N HCl. The pH of the acid phase was increased (about 13) with 5N NaOH and solution was extracted three times with DCM. The organic phase was dried with anhydrous Na$_2$SO$_4$.

The solvent was filtered, evaporated under reduced pressure and the residue was purified by flash chromatography (SiO$_2$, CHCl$_3$/MeOH=85/15).

Compound (19) thus obtained was purified as disclosed in Table 2, obtaining 9.5 g of solid.

Method B

First Step:

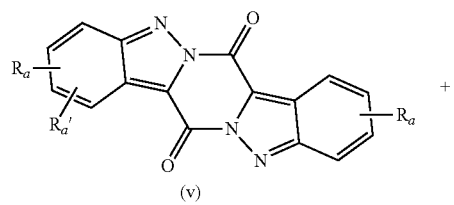

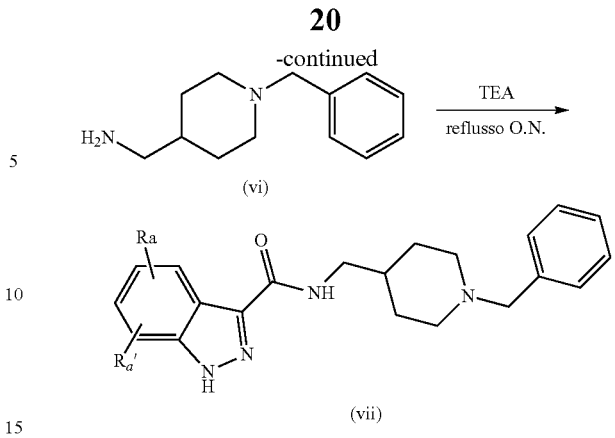

To a suspension of a convenient compound (v) (2.13 g; 0.0061 moles) in toluene (50 ml) was added drop wise a solution of 1-(1-benzylpiperidin-4-yl)methanamine (compound vi; 2.52 g; 0.012 moles), prepared as described in WO 94/10174, and triethylamine (TEA; 3.2 ml; 0.023 moles) in toluene (10 ml). The reaction mixture was refluxed for 12 hours, and then filtered. Solvent was removed by evaporation under reduced pressure and residue was taken up with ethyl acetate. The organic phase was transferred into a separated funnel, washed with saturated NaHCO$_3$ solution and water, separated out and dried over Na$_2$SO$_4$.

The product obtained (vii) was adequately crystallized.

Second Step:

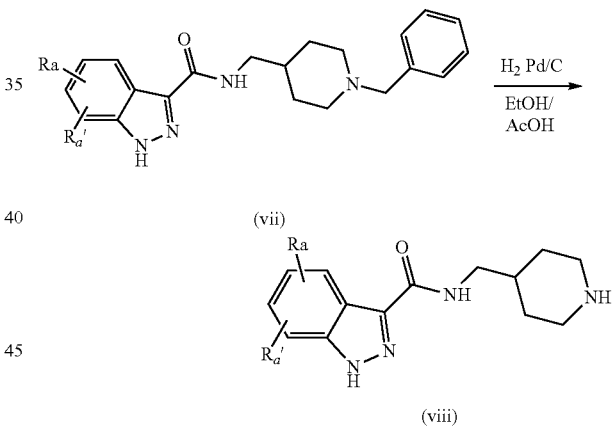

A solution of a convenient N-[(1-benzylpiperidin-4-yl)methyl]-1H-indazole-3-carboxamide (compound vii; 0.506 g; 1.34 mmol) in absolute ethanol (8 ml) and glacial acetic acid (0.8 ml) was hydrogenated in a micro reactor continuous flow system (H-Cube) using CartCart Pd/C 10% as cartridge. Key parameters of H-Cube were set as follow: temperature 80°; pressure 10 bar; flow 1 ml/minute.

After three hours, the solution was concentrated by reduced pressure, diluted with water and transferred into a separating funnel. The aqueous phase was then washed with ethyl acetate, made alkaline with 1N NaOH and extracted with ethyl acetate. The organic layers were collected, dried over Na$_2$SO$_4$ and solvent was removed by evaporation under reduced pressure.

The solid thus obtained was dried in a stove under vacuum to give 0.27 g of the desired substituted N-(piperidin-4-ylmethyl)-1H-indazole-3-carboxamide (viii), which was used without any further purification.

Third Step:

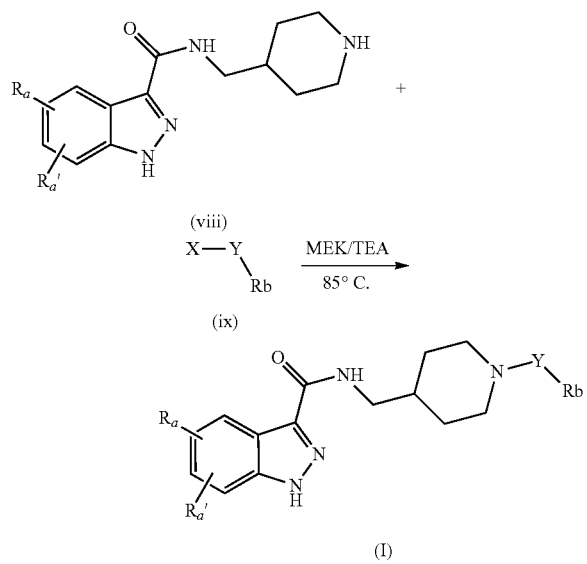

To a solution of (viii) (0.75 mmol; 215 mg) in methyl-ethyl-ketone (MEK; 9 ml) stirred at 85° C., the convenient halogenated compound (ix; 1.05 Eq) and triethylamine (TEA; 210 μl; 2 Eq) were added drop wise. The reaction mixture was refluxed for 8 hours, then cooled and diluted with ethyl acetate. The organic layer was washed with a saturated NH$_4$Cl solution and water. The organic phase was separated out and dried over Na$_2$SO$_4$.

The solvent was removed by evaporating under reduced pressure, and the product (I) was purified as described below.

For example, compound (2) can be prepared according to method B as described below:

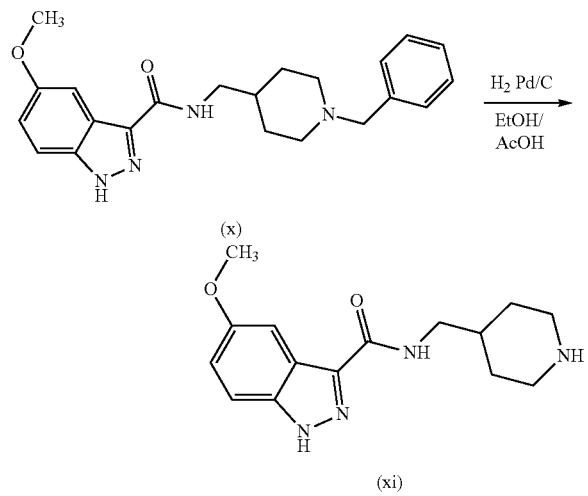

A solution of N-[(1-benzylpiperidin-4-yl)methyl]-5-methoxy-1H-indazole-3-carboxamide (compound x; 0.506 g; 1.34 mmol) in absolute ethanol (8 ml) and glacial acetic acid (0.8 ml) was hydrogenated in a micro reactor continuous flow system (H-Cube) using CartCart Pd/C 10% as cartridge. Key parameters of H-Cube were set as follow: temperature 80°; pressure 10 bar; flow 1 ml/minute.

After three hours, the solution was concentrated by reduced pressure, diluted with water and transferred into a separating funnel. The aqueous phase was then washed with ethyl acetate, made alkaline with 1N NaOH and extracted with ethyl acetate. The organic layers were collected, dried over Na$_2$SO$_4$ and solvent was removed by evaporation under reduced pressure.

The solid thus obtained was dried in a stove under vacuum to give 0.27 of the desired 5-methoxy-N-(piperidin-4-ylmethyl)-1H-indazole-3-carboxamide (xi), which was used without any further purification.

$^1$H NMR (DMSO-d$_6$-300 MHz): δ 13.43 (br. s., 1H), 8.27 (t, J=6.13 Hz, 1H), 7.56 (d, J=2.01 Hz, 1H), 7.51 (dd, J=0.55, 8.96 Hz, 1H), 7.06 (dd, J=2.47, 9.06 Hz, 1H), 6.81 (br. s., 1H), 3.81 (s, 3H), 3.19 (t, J=6.22 Hz, 2H), 3.04 (d, J=5.12 Hz, 2H), 2.93 (s, 3H), 2.85 (d, J=11.34 Hz, 2H), 2.38 (t, J=6.77 Hz, 2H), 1.91 (t, J=10.61 Hz, 2H), 1.45-1.72 (m, 3H), 1.04-1.34 (m, 2H).

[M.M.+H$^+$] calculated 289.1665; [M.M.+H$^+$] found 289.1648.

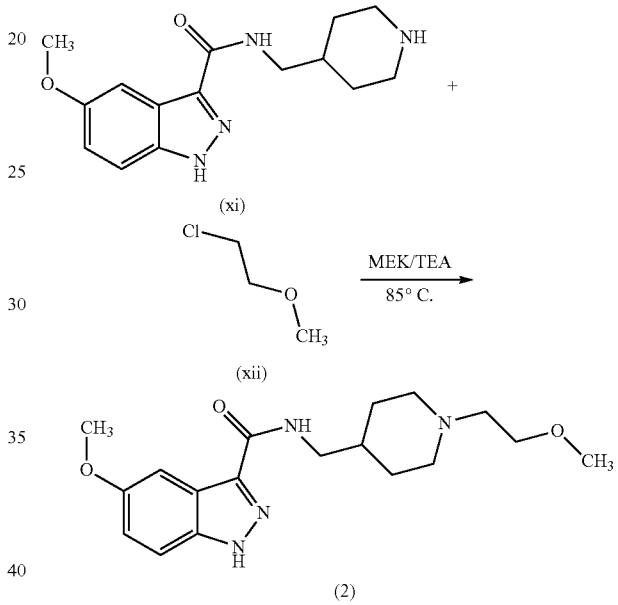

To a solution of (xi) (0.75 mmol; 215 mg) in methyl-ethyl-ketone (MEK; 9 ml) stirred at 85° C., 1-chloro-2-methoxy-ethane (xii; 1.05 Eq) and triethylamine (TEA; 210 μl; 2 Eq) were added drop wise. The reaction mixture was refluxed for 8 hours, then cooled and diluted with ethyl acetate. The organic layer was washed with a saturated NH$_4$Cl solution and water. The organic phase was separated out and dried over Na$_2$SO$_4$.

The solvent was removed by evaporating under reduced pressure, and compound (2) was purified as described below in Table 2.

Method C

First Step:

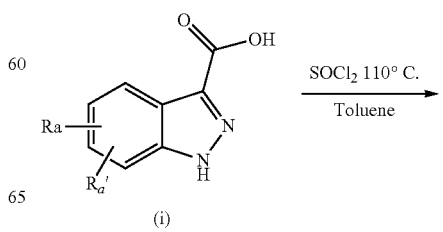

Method D

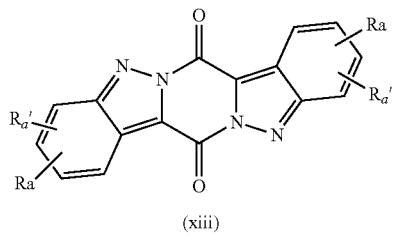

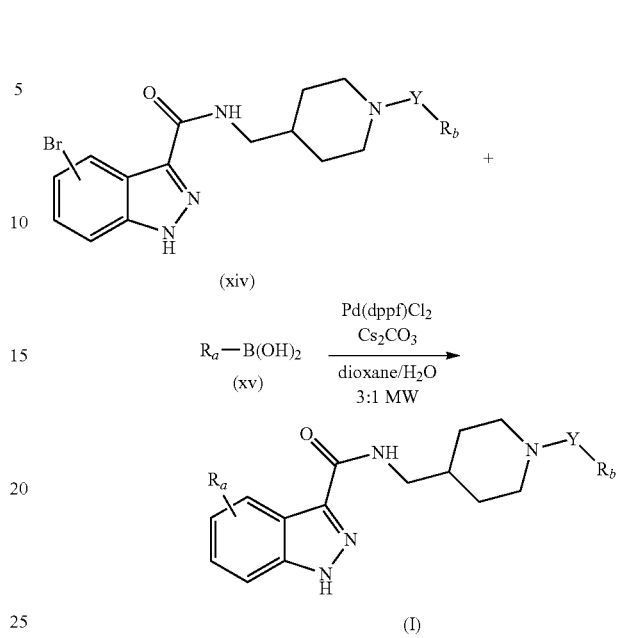

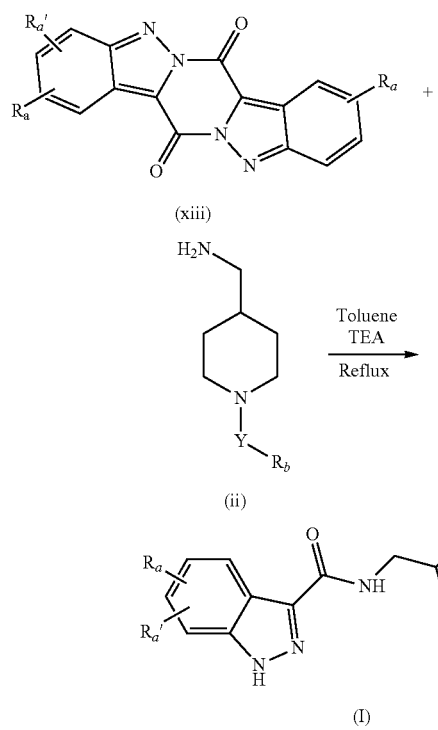

Thionyl chloride (SOCl$_2$; 9.3 ml; 0.128 moles) was added to a suspension of a convenient substituted 1H-indazole-3-carboxylic acid (compound i; 2.36 g; 0.0123 moles) in toluene (77 ml), and the reaction mixture was refluxed for 4 hours. The solvent was removed by evaporation under reduced pressure and the residue was taken up twice in toluene to give 2.13 g of the desired product (xiii) 2,10-substituted 7H,14H-pyrazino[1,2-b:4,5-b']di-indazole-7,14-dione.

Second Step:

To a suspension of (xiii) (5.2 mmol) in toluene (40 ml), a solution of the convenient amine (ii; 2,1 Eq) and triethylamine (TEA; 3,6 Eq; 2.6 ml) was added drop wise. The mixture reaction was refluxed for 8 hours, then cooled and stirred in 2N HCl (20 ml) for 8 hours. The suspension was transferred in a separating funnel and aqueous phase was separating out and made alkaline with 1N NaOH.

The solvent was removed by evaporating under reduced pressure, and the product (I) was purified as described below.

A solution of product (xiv), a conveniently substituted arylboronic acid (compound xv), [1,1'-bis(diphenylphosphino)ferrocene]-dichloro-palladium(II) [Pd(dppf)Cl$_2$], caesium carbonate in 1,4-dioxane and water (ratio 3:1) was subjected to microwave irradiation.

Program was set as follows:
3'; T$_1$=160° C., T$_2$=130° C.; max power 300 W
45'; T$_1$=160° C., T$_2$=130° C.; max power 300 W
5'; T$_1$=20° C., T$_2$=15° C.

After one cycle of microwave irradiation, solvents were removed by evaporating under reduce pressure and the reaction mixture was diluted with a solution of chloroform and methanol in a 2:1 ratio and filtered.

Products (I) thus obtained were purified as described below.

Purification Methods

Compounds of formula (I), obtained according to one of the previously disclosed methods A to D, can be purified with one of the following techniques (a)-(c).
(a) Flash Chromatography on Silica Gel.
Flash chromatography was carried out with a Biotage Flash Master Personal system on 20-45 μm silica cartridge or Grace Reveleris flash chromatography system with 40 μM silica cartridge.
Flow=60 ml/min.
The solvents used as eluents are methanol and chloroform.
(b) Crystallization
A different crystallization solvent was used depending on the compound to be purified. The solvents are shown in the following Table 2.
(c) Preparative LC/MS System.
LC/MS system consisted of a Waters 2767 Sample manager, a Waters 2478 dual λ absorbance detector and a Waters Micromass ZQ single quadrupole mass spectrometer with an electrospray ionization (ESI) source. The column used was a X-Bridge Prep C18 5 μm with 19×10 mm (Waters) pre-column. Fraction collection was available from the system software MassLynx™ v. 4.1. Detection wavelength was set to 230 nm and temperature to 25° C.

The sample was dissolved (50 mg/ml) in DMSO/CH$_3$CN in 1:1 ratio. The mobile phase was:
channel A=CH$_3$CN+0.1% formic acid (Eluent A)
channel B=H$_2$O+0.1% formic acid (Eluent B)
flow=40 ml/min
gradient=minimum and maximum percentage of eluent A reached in 15 minutes are showed in following Table 2.

The following Table 2 shows both the preparation and the purification method for each compound of formula (I) as listed in Table 1 and the monoisotopic mass for each compound.

TABLE 2

| N° | Preparation method | Purification method | Parameters or solvent used for the purification | MM founded [M + H$^+$] | MM calculated [M + H$^+$] |
|---|---|---|---|---|---|
| 1 | B | (b) | AcOEt | 347.1677 | 347.1729 |
| 2 | B | (b) | EtOH/AcOEt | 347.2080 | 347.2083 |
| 3 | B | (b) | EtOH abs/AcOEt | 361.1856 | 361.1876 |
| 4 | D | (c) | 2-40 | 394.2241 | 394.2238 |
| 5 | D | (c) | 2-40 | 424.2350 | 424.2343 |
| 6 | D | (c) | 10-45 | 411.2196 | 411.2191 |
| 7 | D | (c) | 2-27 | 408.2397 | 408.2394 |
| 8 | D | (c) | 15-50 | 429.2105 | 429.2097 |
| 9 | D | (c) | 10-45 | 393.2290 | 393.2285 |
| 10 | D | (c) | 10-45 | 424.2350 | 424.2343 |
| 11 | D | (c) | 10-34 | 409.2247 | 409.2234 |
| 12 | D | (c) | 15-43 | 423.2400 | 423.2391 |
| 13 | D | (c) | 20-55 | 407.2449 | 407.2442 |
| 14 | D | (c) | 10-34 | 424.2340 | 424.2343 |
| 15 | D | (c) | 10-34 | 424.2343 | 424.2343 |
| 16 | D | (c) | 20-55 | 407.2453 | 407.2447 |
| 17 | D | (c) | 10-34 | 437.2190 | 437.2189 |
| 18 | D | (c) | 20-55 | 473.2360 | 473.2364 |
| 19 | A | (b) | THF/H$_2$O | 395.1064 | 395.1077 |

MM: monoisotopic mass
AcOEt: ethyl acetate
EtOH: ethanol
EtOH abs: absolute ethanol
THF: tetrahydrofurane
H$_2$O: water

TABLE 3

| N° | 1H-NMR peaks |
|---|---|
| 1 | DMSO-d6; δ 13.95 (br. s., 2H), 8.24 (t, J = 6.06 Hz, 1H), 7.38-7.62 (m, 2H), 6.86-7.13 (m, 1H), 3.81 (s, 3H), 3.18 (t, J = 6.16 Hz, 2H), 2.94 (d, J = 11.10 Hz, 2H), 2.74 (s, 2H), 1.99 (t, J = 10.90 Hz, 2H), 1.45-1.66 (m, 3H), 1.11-1.35 (m, 2H) |
| 2 | DMSO-d6; δ 13.41 (br. s., 1H), 8.25 (t, J = 6.07 Hz, 1H), 7.56 (d, J = 2.50 Hz, 1H), 7.51 (d, J = 9.06 Hz, 1H), 7.06 (dd, J = 2.50, 9.05 Hz, 1H), 3.81 (s, 3H), 3.41 (t, J = 5.97 Hz, 2H), 3.23 (s, 3H), 3.19 (t, J = 6.26 Hz, 2H), 2.85 (d, J = 11.56 Hz, 2H), 2.43 (t, J = 5.97 Hz, 2H), 1.79-2.06 (m, 2H), 1.48-1.73 (m, 3H), 0.99-1.39 (m, 2H) |
| 3 | DMSO-d6; δ 8.24 (t, J = 6.04 Hz, 1H), 7.46-7.61 (m, 2H), 7.03 (dd, J = 2.60, 8.70 Hz, 1H), 3.81 (s, 3H), 3.18 (t, J = 6.31 Hz, 2H), 2.83 (d, J = 11.25 Hz, 2H), 2.40-2.48 (m, 2H), 2.05-2.16 (m, 2H), 1.78-1.94 (m, 2H), 1.49-1.68 (m, 3H), 1.12-1.29 (m, 2H) |
| 4 | DMSO-d$_6$; δ 13.71 (br. s., 1H), 8.90 (dd, J = 0.82, 2.47 Hz, 1H), 8.58 (d, J = 1.56, 4.67 Hz, 1H), 8.42-8.44 (m, 1H), 8.40 (t, J = 6.00 Hz, 1H), 8.09 (ddd, J = 1.65, 2.42, 8.00 Hz, 1H), 7.70-7.81 (m, 2H), 7.51 (ddd, J = 0.82, 4.76, 7.96 Hz, 1H), 3.37-3.44 (m, 2H), 3.14-3.24 (m, J = 5.90, 5.90 Hz, 5H), 2.84 (d, J = 11.53 Hz, 2H), 2.43 (t, J = 6.04 Hz, 2H), 1.82-1.99 (m, 2H), 1.47-1.74 (m, 3H), 1.09-1.29 (m, 2H) |
| 5 | DMSO-d$_6$; δ 13.66 (br. s., 1H), 8.47 (d, J = 5.85 Hz, 1H), 8.33-8.42 (m, 2H), 8.24 (dd, J = 0.91, 1.65 Hz, 1H), 7.66 (dd, J = 0.91, 8.60 Hz, 1H), 7.53 (dd, J = 1.65, 8.60 Hz, 1H), 7.19 (d, J = 5.67 Hz, 1H), 3.48 (s, 3H), 3.38-3.45 (m, 2H), 3.15-3.25 (m, 5H), 2.88 (d, J = 11.34 Hz, 2H), 2.48 (t, J = 6.00 Hz, 2H), 1.98 (t, J = 10.89 Hz, 2H), 1.47-1.73 (m, 3H), 1.09-1.31 (m, 2H) |
| 6 | DMSO-d$_6$; δ 13.55 (s, 1H), 8.25-8.40 (m, 2H), 7.70 (dd, J = 0.73, 8.78 Hz, 1H), 7.50-7.63 (m, 2H) 7.38-7.49 (m, 1H), 7.28-7.38 (m, 2H), 3.40 (t, J = 5.95 Hz, 2H), 3.12-3.25 (m, J = 6.60 Hz, 5H), 2.84 (d, J = 11.34 Hz, 2H), 2.42 (t, J = 6.04 Hz, 2H), 1.82-1.99 (m, 2H), 1.46-1.72 (m, 3H), 1.06-1.28 (m, 2H) |
| 7 | DMSO-d$_6$; δ 13.68 (br. s., 1H), 8.77 (d, J = 1.83 Hz, 1H), 8.32-8.43 (m, 2H), 7.98 (dd, J = 2.47, 7.96 Hz, 1H), 7.73 (d, J = 1.28 Hz, 2H), 7.37 (d, J = 8.05 Hz, 1H), 3.41 (t, J = 5.95 Hz, 2H), 3.23 (s, 5H), 2.85 (d, J = 11.34 Hz, 2H), 2.53 (s, 3H), 2.43 (t, J = 5.95 Hz, 2H), 1.79-2.01 (m, 2H), 1.44-1.74 (m, 3H), 1.07-1.33 (m, 2H) |
| 8 | DMSO-d$_6$; δ 13.09 (s, 1H), 8.23-8.42 (m, 2H), 7.72 (dd, J = 0.82, 8.69 Hz, 1H), 7.55 (td, J = 1.76, 8.74 Hz, 1H), 7.24-7.49 (m, 3H), 3.40 (t, J = 6.04 Hz, 2H), 3.22 (s, 3H), 3.18 (d, J = 6.40 Hz, 2H), 2.84 (d, J = 11.53 Hz, 2H), 2.42 (t, J = 5.95 Hz, 2H), 1.82-2.02 (m, 2H), 1.41-1.71 (m, 3H), 1.06-1.31 (m, 2H) |
| 9 | DMSO-d$_6$; δ 13.65 (br. s., 1H), 8.40 (t, J = 1.28 Hz, 1H), 8.36 (t, J = 6.13 Hz, 1H), 7.65-7.75 (m, 4H) 7.44-7.53 (m, 2H), 7.32-7.41 (m, 1H), 3.40 (t, J = 6.04 Hz, 2H), 3.12-3.27 (m, J = 6.00, 6.00 Hz, 5H), 2.84 (d, J = 11.34 Hz, 2H), 2.42 (t, J = 6.04 Hz, 2H), 1.83-1.97 (m, 2H), 1.49-1.71 (m, 3H), 1.09-1.31 (m, 2H) |
| 10 | DMSO-d$_6$; δ 13.71 (br. s., 1H), 8.49 (d, J = 1.65 Hz, 1H), 8.43 (dd, J = 0.91, 1.65 Hz, 1H), 8.40 (t, J = 6.13 Hz, 1H), 8.30 (d, J = 2.74 Hz, 1H), 7.78 (dd, J = 1.60, 8.70 Hz, 1H), 7.73 (dd, J = 0.90, 8.70 Hz, 1H), 7.62 (dd, J = 1.83, 2.74 Hz, 1H), 3.94 (s, 3H), 3.40 (t, J = 6.04 Hz, 2H), 3.10-3.26 (m, J = 11.53 Hz, 2H), 2.43 (t, J = 5.95 Hz, 2H), 1.82-2.00 (m, 2H), 1.44-1.73 (m, 3H), 1.05-1.31 (m, 2H) |
| 11 | DMSO-d6; δ 13.53 (br. s., 1H), 9.52 (br. s., 1H), 8.32 (t, J = 6.13 Hz, 1H), 8.29 (t, J = 1.28 Hz, 1H), 7.63 (d, J = 1.28 Hz, 2H), 7.49 (d, J = 8.78 Hz, 2H), 6.87 (d, J = 8.60 Hz, 2H), 3.40 (t, J = 5.95 Hz, 2H), 3.22 (s, 3H), 3.15-3.21 (m, 2H), 2.84 (d, J = 11.53 Hz, 2H), 2.42 (t, J = 5.95 Hz, 2H), 1.91 (t, J = 10.61 Hz, 2H), 1.43-1.72 (m, 3H), 1.03-1.33 (m, 2H) |

TABLE 3-continued

| N° | 1H-NMR peaks |
|---|---|
| 12 | DMSO-d6; δ 13.20 (s, 1H), 8.18-8.40 (m, 2H), 7.49-7.73 (m, 4H), 6.88-7.10 (m, 2H), 3.81 (s, 3H), 3.40 (t, J = 5.95 Hz, 2H), 3.22 (s, 5H), 2.84 (d, J = 11.34 Hz, 2H), 2.42 (t, J = 5.95 Hz, 2H), 1.79-2.01 (m, 2H), 1.43-1.74 (m, 3H), 1.09-1.29 (m, 2H) |
| 13 | DMSO-d6; δ 13.62 (br. s., 1H), 8.29-8.41 (m, 2H), 7.63-7.74 (m, 2H), 7.57 (d, J = 8.05 Hz, 2H), 7.29 (d, J = 7.87 Hz, 2H), 3.40 (t, J = 5.95 Hz, 2H), 3.22 (s, 5H), 2.84 (d, J = 11.34 Hz, 2H), 2.42 (t, J = 5.95 Hz, 2H), 2.36 (s, 3H), 1.80-2.02 (m, 2H), 1.43-1.70 (m, 3H), 1.05-1.31 (m, 2H) |
| 14 | DMSO-d6; δ 8.24-8.38 (m, 2H), 8.18 (dd, J = 1.83, 4.94 Hz, 1H), 7.76 (dd, J = 1.83, 7.32 Hz, 1H) 7.62-7.69 (m, 1H), 7.46-7.58 (m, 1H), 7.11 (dd, J = 4.94, 7.14 Hz, 1H), 3.89 (s, 3H), 3.40 (t, J = 5.95 Hz, 2H), 3.22 (s, 5H), 2.84 (d, J = 11.53 Hz, 2H), 2.42 (t, J = 6.04 Hz, 2H), 1.82-1.97 (m, 2H), 1.47-1.72 (m, 3H), 1.06-1.29 (m, 2H) |
| 15 | DMSO-d6; δ 13.36 (s, 1H), 8.47 (dd, J = 0.73, 2.56 Hz, 1H), 8.26-8.37 (m, 2H), 8.01 (dd, J = 2.60, 8.60 Hz, 1H), 7.70 (dd, J = 1.00, 8.80 Hz, 1H), 7.65 (dd, J = 1.80, 8.80 Hz, 1H), 6.93 (dd, J = 0.73, 8.60 Hz, 1H), 3.91 (s, 3H), 3.40 (t, J = 6.04 Hz, 2H), 3.22 (s, 5H), 2.84 (d, J = 11.34 Hz, 2H), 2.42 (t, J = 6.04 Hz, 2H), 1.80-2.01 (m, 2H), 1.47-1.74 (m, 3H), 1.02-1.35 (m, 2H) |
| 16 | DMSO-d6; δ 13.59 (s, 1H), 8.34 (t, J = 6.13 Hz, 1H), 8.06 (dd, J = 1.56, 0.82 Hz, 1H), 7.65 (dd, J = 0.73, 8.60 Hz, 1H), 7.39 (dd, J = 1.65, 8.60 Hz, 1H), 7.35-7.20 (m, 1H), 3.40 (t, J = 5.95 Hz, 2H), 3.22 (s, 5H), 2.84 (d, J = 11.53 Hz, 2H), 2.42 (t J = 6.04 Hz, 2H), 2.23 (s, 3H), 1.90 (t, J = 10.61 Hz, 2H), 1.50-1.70 (m, 3H), 1.10-1.30 (m, 2H) |
| 17 | DMSO-d6; δ 13.72 (br.s, 1H), 8.49-8.29 (m, 1H), 8.33 (t, J = 6.04 Hz, 1H), 7.83-8.03 (m, 2H) 7.78-7.62 (m, 2H), 7.51-7.61 (m, 2H), 3.41 (t, J = 6.04 Hz, 2H), 3.22 (s, 5H), 2.84 (d, J = 11.34 Hz, 2H), 2.43 (t J = 5.95 Hz, 2H), 1.91 (t, J = 10.70 Hz, 2H), 1.71-1.53 (m, 3H), 1.31-1.11 (m, 2H) |
| 18 | DMSO-d6; δ 13.56 (s, 1H), 8.36-8.16 (m, 2H), 7.72-7.52 (m, 1H), 7.50 (dd, J = 8.78, 1.65 Hz 1H), 7.41 (dd J = 11.53, 9.33 Hz, 1H), 7.25 (dd J = 12.99, 7.14 Hz, 1H), 4.05 (q, J = 6.95 Hz, 2H), 3.40 (t, J = 5095 Hz, 2H), 3.29-3.09 (m, 5H), 2.83 (d J = 11.34 Hz, 2H), 2.42 (t, J = 5.95 Hz, 2H), 2.00-1.80 (m, 2H), 1.70-1.50 (m, 3H), 1.24 (s, 5H) |
| 19 | DMSO-d$_6$; δ 13.74 (br. s., 1H), 8.42 (t, J = 6.07 Hz, 1H), 8.31 (dd, J = 1.83, 0.67 Hz, 1H), 7.61 (dd, J = 8.70, 0.70 Hz, 1H), 7.53 (dd, J = 8.70, 1.70 Hz, 1H), 3.41 (t, J = 5.97 Hz, 2H), 3.22 (s, 3H), 3.13-3.21 (m, 2H), 2.78-2.94 (m, 2H), 2.30-2.47 (m, 2H), 1.82-2.09 (m, 2H), 1.39-1.77 (m, 3H), 1.08-1.30 (m, 2H) |

DMSO: dimethyl sulfoxide

The compounds 20 to 44 were prepared as described hereinbelow.

Synthesis of Compound 20—Ethyl [4-({[(5-bromo-6-methoxy-1H-indazol-3-yl) carbonyl]amino}methyl)piperidin-1-yl]acetate 20a) Ethyl [4-(aminomethyl)piperidin-1-yl]acetate To a stirred solution of N-[phenylmethylidene]-1-(piperidin-4-yl)methanamine (22 g, 0.109 moles (prepared as described in WO2004/101548) in absolute ethanol (150 ml), ethyl bromoacetate (12 mL, 0.109 moles) and potassium carbonate (33 g, 0.24 moles) were added. The solution was heated to reflux for 8 hours, then was cooled and concentrated by evaporating the solvent under reduced pressure. The reaction mixture was diluted with 3N HCl (150 mL) and stirred at room temperature for 2 hours. The acid solution was then washed with ethyl acetate and made alkaline by adding $Na_2CO_3$. The aqueous phase was extracted with three portions of dichloromethane, which were reunited and dried over $Na_2SO_4$. The solvent was removed by evaporating under reduced pressure and the resulting product ethyl [4-(aminomethyl)piperidin-1-yl]acetate 20a was used as such without any further purification.

MS: 201 m/z (M+H+).

1-Hydroxybenzotriazole (HOBt, 2.43 g, 14.2 mmoles) and N,N'-dicyclohexylcarbodiimide (DCC, 2.93 g, 14.2 mmoles) were added to a solution of 5-bromo-6-methoxy-1H-indazole-3-carboxylic acid (3.5 g, 12.9 mmoles) in DMF (40 mL) at 0° C. After 1 hour, a solution of compound 20a (2.6 g, 12.9 mmoles) in DMF (25 mL) was added at the same temperature. The mixture was stirred at 0° C. for 2 hours then was left to reach room temperature during the night. The mixture was diluted with EtOAc and the solid was removed by filtration. The solution was extracted three times with hydrochloric acid (HCl) 2N. The pH of the acid phase was increased (about 13) with 5N NaOH and the solution was extracted three times with dichloromethane (DCM). The organic phase was dried over anhydrous $Na_2SO_4$ and the solvent was filtered and evaporated under reduced pressure providing 1.6 g (3.5 mmoles, 27% yield) of ethyl [4-({[(5-bromo-6-methoxy-1H-indazol-3-yl)carbonyl]amino}methyl)piperidin-1-yl]acetate (compound 20).

$^1$H NMR (300 MHz, DMSO-d6) δ=13.46 (br. s., 1H), 8.35 (t, J=6.2 Hz, 1H), 8.30 (s, 1H), 7.12 (s, 1H), 4.07 (q, J=7.3 Hz, 2H), 3.93 (s, 3H), 3.16 (s, 4H), 2.81 (d, J=11.0 Hz, 2H), 2.19-2.03 (m, 2H), 1.70-1.44 (m, 3H), 1.31-1.04 (m, 5H)

MS: 453 m/z (M+H)+.

Synthesis of Compound 21—{4-[({([6-methoxy-5-(pyridin-3-yl)-1H-indazol-3-yl]carbonyl}amino)methyl]piperidin-1-yl}acetic acid formiate hydrate A solution of compound 20 (200 mg, 0.44 mmoles), pyridin-3-ylboronic acid (217 mg, 1.77 mmoles), [1,1-bis(diphenylphosphino)ferrocene]-dichloro-palladium(II) [Pd(dppf)Cl$_2$] (81 mg, 0.11 mmoles) and caesium carbonate (575 mg, 1.76 mmoles) in 1,4-dioxane and water (ratio 3:1, 8 mL) was subjected to microwave irradiation as follows:

Time period=3'; $T_1$=160° C., $T_2$=130° C.; max power 300 W

Time period=45'; $T_1$=160° C., $T_2$=130° C.; max power 300 W

Time period=5'; $T_1$=20° C., $T_2$=15° C.

After one cycle of microwave irradiation, solvents were removed by evaporating under reduce pressure and the reaction mixture was diluted with a solution of methanol (20 mL), filtered over Celite and dried under vacuum. The crude product was filtered on a silica cartridge and washed with chloroform and methanol in a 1:1 ratio. The resulting solid was dissolved in DMSO and purified via preparative HPLC (channel A=CH$_3$CN+0.1% formic acid; channel B=H$_2$O+0.1% formic acid: flow=40 ml/min; gradient=2%-40% of eluent A in 15 minutes), providing {4-[({[6-methoxy-5-(pyridin-3-yl)-1H-indazol-3-yl]carbonyl}amino)methyl]piperidin-1-yl}acetic acid formate hydrate 21 (67 mg, 36% yield).

$^1$H NMR (300 MHz, DMSO-d6) δ=13.44 (br. s., 1H), 8.66 (dd, J=0.9, 2.4 Hz, 1H), 8.54 (dd, J=1.8, 4.8 Hz, 1H), 8.42 (t, J=6.2 Hz, 1H), 8.01 (s, 1H), 7.91-7.85 (m, 1H), 7.45 (ddd, J=0.9, 4.8, 7.8 Hz, 1H), 7.13 (s, 1H), 3.86 (s, 3H), 3.41 (br. s., 1H), 3.30-3.00 (m, 6H), 2.54 (s, 2H), 1.73 (d, J=11.0 Hz, 3H), 1.52-1.28 (m, 2H)

MS: 424 m/z (M+H)$^+$.

Synthesis of Compound 22—{4-[({[6-methoxy-5-(5-methoxy pyridin-3-yl)-1H-indazol-3-yl]carbonyl}amino)methyl]piperidin-1-yl}acetic acid hydrate {4-[({[6-methoxy-5-(5-methoxypyridin-3-yl)-1H-indazol-3-yl]carbonyl}amino)methyl]-piperidin-1-yl}acetic acid hydrate 22 was prepared, according to the procedure described for compound 21, starting from (5-methoxypyridin-3-yl)boronic acid and using the following preparative HPLC parameters for the purification: channel A=CH$_3$CN+0.1% formic acid; channel B=H$_2$O+0.1% formic acid: flow=40 ml/min; gradient=10%-45% of eluent A in 15 minutes. Yield: 33 mg, 17%.

$^1$H NMR (300 MHz, DMSO-d6) δ=13.46 (br. s., 1H), 8.42 (t, J=6.0 Hz, 1H), 8.26 (dd, J=2.0, 6.8 Hz, 2H), 8.02 (s, 1H), 7.43 (dd, J=1.6, 2.7 Hz, 1H), 7.13 (s, 1H), 3.88 (s, 3H), 3.86 (s, 3H), 3.98 (br. s., 1H), 3.30-3.01 (m, 6H), 2.66-2.53 (m, 2H), 1.73 (d, J=10.6 Hz, 3H), 1.40 (q, J=11.6 Hz, 2H)

MS: 454 m/z (M+H)$^+$.

Synthesis of Compound 23—{4-[({[5-(2,3-difluorophenyl)-6-methoxy-1H-indazol-3-yl]carbonyl}amino)methyl]piperidin-1-yl}acetic acid hydrate {4-[({[5-(2,3-difluorophenyl)-6-methoxy-1H-indazol-3-yl]carbonyl}amino)methyl]piperidin-1-yl}acetic acid hydrate 23 was prepared, according to the procedure described for compound 21, starting from (2,3-difluorophenyl)boronic acid and using the following preparative HPLC parameters for the purification: channel A=CH$_3$CN+0.1% formic acid; channel B=H$_2$O+0.1% formic acid: flow=40 ml/min; gradient=15%-50% of eluent A in 15 minutes. Yield: 48 mg, 24%.

$^1$H NMR (300 MHz, DMSO-d6) δ=13.50 (br. s., 1H), 8.42 (t, J=6.0 Hz, 1H), 7.97 (s, 1H), 7.53-7.36 (m, 1H), 7.33-7.16 (m, 2H), 7.13 (s, 1H), 4.13 (br. s., 1H), 3.84 (s, 3H), 3.30-3.08 (m, 6H), 2.65-2.53 (m, 2H), 1.72 (d, J=11.0 Hz, 3H), 1.40 (q, J=11.7 Hz, 2H)

MS: 459 m/z (M+H)$^+$.

Synthesis of Compound 24—4-[4-({[(5-methoxy-1H-indazol-3-yl)carbonyl]amino}methyl)piperidin-1-yl]butanoic acid 24a) Tert-butyl 4-({[(5-methoxy-1H-indazol-3-yl)carbonyl]amino}methyl)piperidine-1-carboxylate Tert-butyl 4-({[(5-methoxy-1H-indazol-3-yl)carbonyl]amino}methyl) piperidine-1-carboxylate 24a was prepared, according to the procedure described for compound 20, from 5-methoxy-1H-indazole-3-carboxylic acid and tert-butyl 4-(aminomethyl)piperidine-1-carboxylate. Yield: 35.2 g, 96%.

MS: 389 m/z (M+H)$^+$.

24b) 5-Methoxy-N-(piperidin-4-ylmethyl)-1H-indazole-3-carboxamide hydrochloride

2 M HCl in Et$_2$O (1.8 L) was added to a solution of compound 24a (92.8 g, 0.24 moles) in MeOH (500 mL). The mixture was stirred for 3 hours at room temperature then the resulting solid was filtered and dried to give 5-methoxy-N-(piperidin-4-ylmethyl)-1H-indazole-3-carboxamide hydrochloride 24b (61.1 g, 89% yield).

MS: 289 m/z (M+H)$^+$.

24c) Ethyl 4-[4-({[(5-methoxy-1H-indazol-3-yl)carbonyl]amino}methyl) piperidin-1-yl]butanoate A mixture of compound 24b (8 g, 24.6 mmoles) and potassium carbonate (17 g, 123 mmoles) in acetone (250 mL) was refluxed for 1 hour, then ethyl 4-chlorobutanoate (3.62 mL, 25.9 mmoles) was added dropwise. The mixture was refluxed overnight then was cooled and filtered. The resulting solid was dried and purified via preparative HPLC (channel A=CH$_3$CN+0.1% formic acid; channel B=H$_2$O+0.1% formic acid: flow=40 ml/min; gradient=10%-45% of eluent A in 15 minutes) providing 0.9 g (9% yield) of ethyl 4-[4-({[(5-methoxy-1H-indazol-3-yl)carbonyl]amino}methyl)piperidin-1-yl]butanoate 24c.

MS: 403 m/z (M+H)$^+$.

To a solution of compound 24c (744 mg, 1.85 mmoles) in MeOH (10 mL) aqueous NaOH (1 M, 3.7 mL) was added. The solution was refluxed overnight then the organic solvent was removed under vacuum, the residue was diluted with H$_2$O and the pH was adjusted to 5 by adding 1 M HCl. The mixture was kept at 4° C. overnight then the resulting solid was filtered, washed with fresh water and dried under vacuum to give 4-[4-({[(5-methoxy-1H-indazol-3-yl)carbonyl]amino}methyl)piperidin-1-yl]butanoic acid 24 (72 mg, 10% yield).

$^1$H NMR (300 MHz, DMSO-d6) δ=13.54 (br. s., 1H), 11.25 (br. s., 1H), 8.46 (t, J=6.1 Hz, 1H), 7.55 (d, J=2.3 Hz, 1H), 7.52 (d, J=8.9 Hz, 1H), 7.05 (dd, J=2.3, 8.9 Hz, 1H), 3.80 (s, 3H), 3.37 (d, J=12.2 Hz, 2H), 3.23 (t, J=6.1 Hz, 2H), 3.00-2.89 (m, 2H), 2.81 (t, J=11.4 Hz, 2H), 2.32 (t, J=7.1 Hz, 2H), 2.01-1.70 (m, 5H), 1.64-1.41 (m, 2H)

MS: 375 m/z (M+H)$^+$.

Synthesis of Compound 25—{4-[({[5-(Pyrimidin-5-yl)-1H-indazol-3-yl]carbonyl}amino)methyl]piperidin-1-yl} acetic acid hydrate 25a) Tert-butyl 4-({[(5-bromo-1H-indazol-3-yl)carbonyl]amino}methyl)piperidine-1-carboxylate Tert-butyl4-({[(5-bromo-1H-indazol-3-yl)carbonyl]amino}methyl) piperidine-1-carboxylate 25a was prepared, according to the procedure described for compound 20, from 5-bromo-1H-indazole-3-carboxylic acid and tert-butyl 4-(aminomethyl)piperidine-1-carboxylate. Yield: 40.6 g, 87%

MS: 437 m/z (M+H)$^+$.

25b) 5-Bromo-N-(piperidin-4-ylmethyl)-1H-indazole-3-carboxamide hydrochloride

5-Bromo-N-(piperidin-4-ylmethyl)-1H-indazole-3-carboxamide hydrochloride 25b was prepared, according to the procedure described for compound 24b, starting from compound 25a. Yield: 23.8 g, 76%.

MS: 337 m/z (M+H)+.

25c) Ethyl [4-({[(5-bromo-1H-indazol-3-yl)carbonyl]amino} methyl) piperidin-1-yl]acetate A mixture of compound 25b (2 g, 5.4 mmoles) and potassium carbonate (2.3 g, 16.6 mmoles) in DMF (45 mL) was stirred for 1 hour at 70° C. A solution of ethyl bromoacetate (0.89 mL, 8 mmoles) in DMF (5 mL) was added dropwise. After 3 hours at 70° C. the reaction mixture was cooled, diluted with water and extracted three times with EtOAc. The reunited organic phases were dried over $Na_2SO_4$ and concentrated under vacuum. The crude product was purified via flash chromatography (silica, $CHCl_3$:MeOH 95:5) providing 710 mg (31% yield) of ethyl [4-({[(5-bromo-1H-indazol-3-yl)carbonyl]amino}methyl) piperidin-1-yl]acetate 25c.

$^1$H NMR (300 MHz, DMSO-d6) δ=13.74 (s, 1H), 8.43 (t, J=6.0 Hz, 1H), 8.32 (dd, J=0.6, 1.9 Hz, 1H), 7.61 (dd, J=0.6, 8.9 Hz, 1H), 7.53 (dd, J=1.9, 8.9 Hz, 1H), 4.07 (q, J=7.1 Hz, 2H), 3.20 (t, J=6.4 Hz, 2H), 3.17 (s, 2H), 2.81 (d, J=11.2 Hz, 2H), 2.22-2.03 (m, 2H), 1.72-1.46 (m, 3H), 1.31-1.08 (m, 5H).

MS: 423 m/z (M+H)+.

4-[({[5-(Pyrimidin-5-yl)-1H-indazol-3-yl]carbonyl}amino)methyl]piperidin-1-yl}acetic acid hydrate 25 was prepared, according to the procedure described for compound 21, from compound 25c and pyrimidin-5-ylboronic acid. The product was purified by crystallization in MeOH. Yield: 43 mg, 18%.

$^1$H NMR (300 MHz, DMSO-d6) δ=13.90 (br. s., 1H), 9.20 (s, 1H), 9.15 (s, 2H), 8.54 (t, J=6.0 Hz, 1H), 8.48 (s, 1H), 8.00-7.56 (m, 2H), 4.63 (br. s., 1H), 3.45-3.01 (m, 6H), 2.60 (t, J=11.3 Hz, 2H), 1.76 (d, J=11.3 Hz, 3H), 1.44 (q, J=11.3 Hz, 2H)

MS: 395 m/z (M+H)+.

Synthesis of Compound 26—{4-[({[5-(3,5-Dimethylisoxazol-4-yl)-1H-indazol-3-yl]carbonyl}amino)methyl]piperidin-1-yl} acetic acid hydrate {4-[({[5-(3,5-Dimethylisoxazol-4-yl)-1H-indazol-3-yl]carbonyl}amino) methyl]piperidin-1-yl}acetic acid hydrate 26 was prepared, according to the procedure described for compound 21, from compound 25c and (3,5-dimethylisoxazol-4-yl)boronic acid. The product was purified by crystallization in MeOH. Yield: 55 mg, 23%.

$^1$H NMR (300 MHz, DMSO-d6) δ=13.84 (br. s., 1H), 8.50 (t, J=5.9 Hz, 1H), 8.10 (s, 1H), 7.72 (d, J=8.6 Hz, 1H), 7.40 (dd, J=1.5, 8.8 Hz, 1H), 4.10 (br. s., 1H), 3.36-3.03 (m, 6H), 2.60 (t, J=11.2 Hz, 2H), 2.41 (s, 3H), 2.22 (s, 3H), 1.75 (d, J=11.2 Hz, 3H), 1.42 (q, J=11.4 Hz, 2H)

MS: 412 m/z (M+H)+.

Synthesis of Compound 27—{4-[({[5-(2,3-dichlorophenyl)-1H-indazol-3-yl]carbonyl}amino)methyl]piperidin-1-yl} acetic acid hydrate {4-[({[5-(2,3-Dichlorophenyl)-1H-indazol-3-yl]carbonyl}amino)methyl]piperidin-1-yl}acetic acid hydrate 27 was prepared, according to the procedure described for compound 21, from compound 25c and (2,3-dichlorophenyl)boronic acid and using the following preparative HPLC parameters for the purification: channel A=$CH_3CN$+0.1% formic acid; channel B=$H_2O$+0.1% formic acid: flow=40 ml/min; gradient=20%-55% of eluent A in 15 minutes. Yield: 42 mg, 15%.

$^1$H NMR (300 MHz, DMSO-d6) δ=13.81 (br. s., 1H), 8.50 (t, J=6.0 Hz, 1H), 8.17 (dd, J=0.9, 1.6 Hz, 1H), 7.78-7.60 (m, 2H), 7.54-7.34 (m, 3H), 4.08 (br. s., 1H), 3.38-2.96 (m, 6H), 2.58 (t, J=11.0 Hz, 2H), 1.74 (d, J=11.0 Hz, 3H), 1.42 (q, J=11.6 Hz, 2H)

MS: 461 m/z (M+H)+.

Synthesis of Compound 28—{4-[({[5-(3-Fluorophenyl)-1H-indazol-3-yl]carbonyl}amino)methyl] piperidin-1-yl} acetic acid hydrate {4-[({[5-(3-Fluorophenyl)-1H-indazol-3-yl]carbonyl}amino)methyl]piperidin-1-yl}acetic acid hydrate 28 was prepared, according to the procedure described for compound 21, from compound 25c and (3-fluorophenyl)boronic acid and using the following preparative HPLC parameters for the purification: channel A=$CH_3CN$+0.1% formic acid; channel B=$H_2O$+0.1% formic acid: flow=40 ml/min; gradient=15%-50% of eluent A in 15 minutes. Yield: 87 mg, 36%.

$^1$H NMR (300 MHz, DMSO-d6) δ=13.71 (br. s., 1H), 8.45 (t, J=6.0 Hz, 1H), 8.41 (s, 1H), 7.86-7.66 (m, 2H), 7.63-7.41 (m, 3H), 7.19 (dddd, J=2.4, 2.6, 6.5, 9.0 Hz, 1H), 4.75 (br. s., 1H), 3.34-3.07 (m, 6H), 2.64-2.53 (m, 2H), 1.75 (d, J=11.0 Hz, 3H), 1.42 (q, J=11.5 Hz, 2H)

MS: 411 m/z (M+H)+.

Synthesis of Compound 29—{4-[({[5-(2,3-difluorophenyl)-1H-indazol-3-yl]carbonyl}amino)methyl] piperidin-1-yl} acetic acid {4-[({[5-(2,3-difluorophenyl)-1H-indazol-3-yl]carbonyl}amino)methyl]piperidin-1-yl}acetic acid 29 was prepared, according to the procedure described for compound 21, starting from compound 25c and (2,3-difluorophenyl)boronic acid and using the following preparative HPLC parameters for the purification: channel A=$CH_3CN$+0.1% formic acid; channel B=$H_2O$+0.1% formic acid: flow=40 ml/min; gradient=15 to 50% of eluent A in 15 minutes. Yield: 20 mg, (11.7%).

$^1$H NMR (300 MHz, DMSO-d6) δ=13.68 (br. s., 1H), 8.51 (t, J=6.1 Hz, 1H), 8.35 (d, J=0.6 Hz, 1H), 7.74 (dd, J=0.7, 8.8 Hz, 1H), 7.61 (td, J=1.7, 8.7 Hz, 1H), 7.51-7.25 (m, 3H), 3.33-3.10 (m, 6H), 2.64-2.53 (m, 2H), 1.74 (d, J=10.5 Hz, 3H), 1.54-1.29 (m, 2H)

Synthesis of Compound 30—{4-[({[5-(5-methoxypyridin-3-yl)-1H-indazol-3-yl]carbonyl}amino) methyl]piperidin-1-yl}acetic acid {4-[({[5-(5-methoxypyridin-3-yl)-1H-indazol-3-yl]carbonyl}amino) methyl]piperidin-1-yl}acetic acid 30 was prepared, according to the procedure described for compound 21, starting from compound 25c and (5-methoxypyridin-3-yl)boronic acid and using the following preparative HPLC parameters for the purification: channel A=$CH_3CN$+0.1% formic acid; channel B=$H_2O$+0.1% formic acid: flow=40 ml/min; gradient=2 to 40% of eluent A in 15 minutes. Yield: 47 mg (27.8%).

$^1$H NMR (300 MHz, DMSO-d6) δ=13.73 (br. s., 1H), 8.54-8.49 (m, 1H), 8.48 (d, J=1.6 Hz, 1H), 8.44-8.39 (m, 1H), 8.30 (d, J=2.7 Hz, 1H), 7.81-7.76 (m, 1H), 7.76-7.69 (m, J=0.7 Hz, 1H), 7.61 (dd, J=1.8, 2.7 Hz, 1H), 3.93 (s, 3H), 3.29-3.12 (m, 6H), 2.69-2.55 (m, 2H), 1.75 (d, J=11.0 Hz, 3H), 1.58-1.27 (m, 2H)

Synthesis of Compound 31—[4-({[(5-ethyl-1H-indazol-3-yl)carbonyl]amino}methyl)piperidin-1-yl] acetic acid A mixture of product 25c (170 mg, 0.4 mmol), vinyl-boronic acid pinacol ester (0.53 mmol), [1,1'-bis(diphenylphosphino)ferrocene]-dichloro-palladium(II) (50 mg, 0.06 mmol), sodium carbonate saturated solution (1.7 mL) in toluene/ethanol (ratio 1:1, 10 mL) was heated in a microwave oven at 150° C., 500 W for 2 h. After filtration over celite, solvents were removed under reduce pressure and the crude product was eluted through a silica gel cartridge with a mixture of chloroform/methanol 1:1 ratio. Solvents were removed under reduced pressure and the resulting crude intermediate was dissolved in ethanol (20 mg/mL) and hydrogenated over a 10% Pd/C cartridge at 30° C., 1 mL/min in a Thales Nano H-CUBE hydrogenetor to obtain [4-({[(5-ethyl-1H-indazol-3-yl)carbonyl]amino}methyl)piperidin-1-yl] acetic acid 31, purified using the following preparative HPLC parameters: channel A=$CH_3CN$+0.1% formic acid; channel B=$H_2O$+0.1% formic acid: flow=40 ml/min; gradient=10 to 45% of eluent A in 15 minutes. Yield 170 mg, (41.0%).

$^1$H NMR (300 MHz, DMSO-d6) δ=13.48 (br. s., 1H), 8.38 (t, J=6.1 Hz, 1H), 7.97 (s, 1H), 7.52 (d, J=8.6 Hz, 1H), 7.28 (dd, J=1.6, 8.6 Hz, 1H), 4.38 (br. s., 1H), 3.33-3.09 (m, 6H), 2.73 (q, J=7.5 Hz, 2H), 2.65-2.53 (m, 2H), 1.83-1.60 (m, 3H), 1.54-1.31 (m, 2H), 1.23 (t, J=7.5 Hz, 3H)

Synthesis of Compound 32—{4-[({[5-(propan-2-yl)-1H-indazol-3-yl]carbonyl}amino)methyl]piperidin-1-yl}acetic acid {4-[({[5-(propan-2-yl)-1H-indazol-3-yl]carbonyl}amino) methyl]piperidin-1-yl}acetic acid 32 was prepared, according to the procedure described for compound 31, starting from 1-methylethylen-boronic acid pinacol ester. Yield=33 mg (7.7%).

$^1$H NMR (300 MHz, DMSO-d6) δ=13.45 (br. s., 1H), 8.38 (t, J=6.1 Hz, 1H), 8.10-7.86 (m, 1H), 7.52 (dd, J=0.5, 8.6 Hz, 1H), 7.32 (dd, J=1.6, 8.8 Hz, 1H), 4.65 (br. s., 1H), 3.29-3.13 (m, 6H), 3.02 (quind, J=6.8, 13.7 Hz, 1H), 2.57 (t, J=11.3 Hz, 2H), 1.73 (d, J=10.8 Hz, 3H), 1.55-1.32 (m, 2H), 1.26 (d, J=7.0 Hz, 6H)

Synthesis of Compound 33—{4-[({[5-(3,6-dihydro-2H-pyran-4-yl)-1H-indazol-3-yl]carbonyl}amino) methyl]piperidin-1-yl} acetic acid {4-[({[5-(3,6-dihydro-2H-pyran-4-yl)-1H-indazol-3-yl] carbonyl}amino) methyl]piperidin-1-yl}acetic acid 33 was prepared, according to the procedure described for compound 31 (without the hydrogenation step), starting from 4-methyl-3,6-dihydro-2H-pyranyl-boronic acid pinacol ester. Yield=150 mg (37.7%).

$^1$H NMR (300 MHz, DMSO-d6) δ=13.65 (br. s., 1H), 8.44 (t, J=5.9 Hz, 1H), 8.15 (s, 1H), 7.71-7.47 (m, 2H), 6.27 (br. s., 1H), 5.78-4.52 (m, 1H), 4.25 (d, J=2.2 Hz, 2H), 3.86 (t, J=5.3 Hz, 2H), 3.34-3.05 (m, 6H), 2.68-2.54 (m, 4H), 1.74 (d, J=10.9 Hz, 3H), 1.42 (q, J=11.5 Hz, 2H).

Synthesis of Compound 34—[4-({[(5-cyclohexyl-1H-indazol-3-yl)carbonyl]amino}methyl)piperidin-1-yl] acetic acid

[4-({[(5-cyclohexyl-1H-indazol-3-yl)carbonyl] amino}methyl)piperidin-1-yl]acetic acid 34, was prepared, according to the procedure described for compound 31, starting from cyclohexenyl-boronic acid pinacol ester. Yield=158 mg (39.6%).

$^1$H NMR (300 MHz, DMSO-d6) δ=13.48 (br. s., 1H), 8.38 (t, J=6.0 Hz, 1H), 7.98 (s, 1H), 7.51 (d, J=8.8 Hz, 1H), 7.30 (dd, J=1.2, 8.7 Hz, 1H), 4.67 (br. s., 1H), 3.24 (d, J=4.8 Hz, 6H), 2.68-2.53 (m, 3H), 1.96-1.58 (m, 8H), 1.54-1.14 (m, 7H)

Synthesis of Compound 35—[4-({[(5-pentyl-1H-indazol-3-yl)carbonyl]amino}methyl)piperidin-1-yl] acetic acid

[4-({[(5-pentyl-1H-indazol-3-yl)carbonyl] amino}methyl)piperidin-1-yl]acetic acid 35 was prepared, according to the procedure described for compound 31, starting from 5-pentyl-boronic acid pinacol ester. Yield=176 mg (45.6%).

$^1$H NMR (300 MHz, DMSO-d6) δ=13.49 (br. s., 1H), 8.38 (t, J=5.9 Hz, 1H), 7.95 (s, 1H), 7.51 (dd, J=0.7, 8.6 Hz, 1H), 7.25 (dd, J=1.5, 8.8 Hz, 1H), 3.20 (s, 6H), 2.69 (t, J=7.4 Hz, 2H), 2.59 (t, J=11.1 Hz, 2H), 1.86-1.15 (m, 11H), 0.93-0.77 (m, 3H).

Synthesis of Compound 36—5-methoxy-N-[(1-{3-[(phenyl carbonyl)amino]propyl}piperidin-4-yl) methyl]-1H-indazole-3-carboxamide

36a) tert-butyl {3-[4-({[(5-methoxy-1H-indazol-3-yl)carbonyl] amino}methyl)piperidin-1-yl] propyl}carbamate A solution of compound 24b (1.37 g, 4.36 mmol) in DMF (45 ml) and triethylamine (1.3 ml, 9.5 mmol) was stirred at 80° C. for 1 h and then was treated with tert-butyl (3-bromopropyl)carbamate (1.7 g, 7.1 mmol). The mixture was stirred overnight at the same temperature. The reaction was then cooled to room temperature and the solvent was removed by evaporation at reduced pressure. The crude tert-butyl {3-[4-({[(5-methoxy-1H-indazol-3-yl)carbonyl] amino}methyl)piperidin-1-yl]propyl}-carbamate 36a was used for the subsequent step without further purifications.

LC-MS: 446.3 $(M+H)^+$.

36b) N-{[1-(3-aminopropyl)piperidin-4-yl]methyl}-5-methoxy-1H-indazole-3-carboxamide A solution of crude tert-butyl {3-[4-({[(5-methoxy-1H-indazol-3-yl)carbonyl]amino}methyl)piperidin-1-yl] propyl}carbamate 36a (approx. 1.8 g) in $CH_2Cl_2$ (15 ml) was treated with trifluoroacetic acid (7 ml) at room temperature overnight. The solution was then poured in water (50 ml) and washed with $CH_2Cl_2$ (3×20 ml). The acid phase was basified and concentrated at reduced pressure. The solid residue was extracted with a mixture of $CH_3Cl/CH_3OH$ in 8/2 ratio (3×20 ml) and the solvent evaporated at reduced pressure. The crude N-{[1-(3-aminopropyl)piperidin-4-yl] methyl}-5-methoxy-1H-indazole-3-carboxamide 36b was used for the next steps without further purifications.

LC-MS: 346.2 $(M+H)^+$.

To a solution of crude N-{[1-(3-aminopropyl)piperidin-4-yl]methyl}-5-methoxy-1H-indazole-3-carboxamide 36b (approx. 350 mg, 1 mmol) in DMSO (1.5 mL) and $CH_2Cl_2$ (10 mL) was added benzoyl chloride (71 µl, 0.61 mmol). The solution was then stirred at room temperature for 2 h. The mixture was then added to water (20 ml) and extracted with $CH_2Cl_2$ (3×10 mL). The combined organic phases was concentrated at reduced pressure and the crude product was purify by flash chromatography on silica gel, using a mixture of CHCl₃/CH₃OH=9:1 as eluent. 5-methoxy-N-[(1-{3-[(phenylcarbonyl)amino]propyl}piperidin-4-yl) methyl]-1H-indazole-3-carboxamide 36 was obtained (71 mg).

¹H NMR (300 MHz, DMSO-d6) δ=13.43 (s, 1H), 8.59-8.47 (t, J=5.31 Hz, 1H), 8.38-8.24 (t, J=6.04 Hz, 1H), 7.90-7.74 (m, 2H), 7.61-7.35 (m, 5H), 7.10-6.99 (dd, J=9.15, 2.56 Hz, 1H), 3.89-3.69 (s, 3H), 3.39-3.12 (m, 6H), 3.11-2.94 (m, 2H), 2.25-1.89 (m, 2H), 1.83-1.53 (m, 5H), 1.36-1.12 (d, J=11.34 Hz, 2H)

LC-MS: 450.25 (MH+)

Synthesis of Compound 37—N-({1-[3-(butanoylamino) propyl]piperidin-4-yl}methyl)-6-methoxy-1H-indazole-3-carboxamide N-({1-[3-(butanoylamino)propyl]piperidin-4-yl}methyl)-5-methoxy-1H-indazole-3-carboxamide 37, was prepared, according to the procedure described for compound 36, starting from butanoyl chloride. Yield=75 mg (36.8%).

¹H NMR (300 MHz, DMSO-d6) δ=13.44 (s, 1H), 8.41-8.26 (t, J=6.11 Hz, 1H), 7.89-7.69 (t, J=5.12 Hz, 1H), 7.58-7.54 (d, J=2.31 Hz, 1H), 7.53-7.47 (dd, J=8.92, 0.66 Hz, 1H), 7.11-6.96 (dd, J=9.08, 2.48 Hz, 1H), 3.80 (s, 3H), 3.52-2.77 (m, 10H), 2.10-1.92 (t, J=7.27 Hz, 2H), 1.81-1.12 (m, 9H), 0.91-0.77 (t, J=7.27, 3H)

LC-MS: 416.27 (MH+)

Synthesis of Compound 38—N-[(1-{3-[(2E)-but-2-enoylamino]propyl}piperidin-4-yl)methyl]-5-methoxy-1H-indazole-3-carboxamide N-[(1-{3-[(2E)-but-2-enoylamino]propyl}piperidin-4-yl) methyl]-5-methoxy-1H-indazole-3-carboxamide 38 was prepared, according to the procedure described for compound 36, starting from (2E)-but-2-enoyl chloride. Yield=45 mg (51.4%).

¹H NMR (300 MHz, DMSO-d6) δ=13.44 (s, 1H), 8.45-8.25 (m, 1H), 8.00-7.75 (m, 1H), 7.60-7.53 (d, J=2.40 Hz, 1H), 7.53-7.47 (d, J=8.90 Hz, 1H), 7.09-7.01 (dd, J=2.70, 2.30 Hz, 1H), 6.67-6.50 (m, 1H), 5.75-6.00 (m, 1H), 3.80 (s, 3H), 3.50-1.00 (m, 20H)

LC-MS: 414.25 (M−H+)

Synthesis of Compound 39—5-methoxy-N-({1-[3-(propanoyl amino)propyl]piperidin-4-yl}methyl)-1H-indazole-3-carboxamide 5-methoxy-N-({1-[3-(propanoylamino)propyl]piperidin-4-yl}methyl)-1H-indazole-3-carboxamide 39, was prepared, according to the procedure described for compound 36, starting from propanoyl chloride. Yield=90 mg (68.8%).

¹H NMR (300 MHz, DMSO-d6) δ=13.28 (s, 1H), 8.17-8.00 (m, 1H), 7.65-7.55 (m, 1H), 7.58-7.54 (d, J=2.20 Hz, 1H), 7.52-7.45 (d, J=9.20 Hz, 1H), 7.10-7.00 (dd, J=9.15, 2.60 Hz, 1H), 3.81 (s, 3H), 3.30-2.85 (m, 8H), 2.11-2.00 (q, J=7.70 Hz, 2H), 1.80-1.52 (m, 6H), 1.40-1.15 (m, 3H), 1.03-0.95 (t, J=7.70 Hz, 3H)

LC-MS: 402.25 (M−H+)

Synthesis of Compound 40—N-({1-[3-(but-2-ynoylamino) propyl]piperidin-4-yl}methyl)-6-methoxy-1H-indazole-3-carboxamide N-({1-[3-(but-2-ynoylamino)propyl]piperidin-4-yl}methyl)-5-methoxy-1H-indazole-3-carboxamide 40 was prepared, according to the procedure described for compound 36, starting from 2-butynoyl chloride. Yield=17 mg (17.1%).

¹H NMR (300 MHz, DMSO-d6) δ=13.34 (s, 1H), 8.52-8.42 (t, J=5.31 Hz, 1H), 8.27-8.18 (t, J=6.04 Hz, 1H), 7.56-7.52 (d, J=2.20 Hz, 1H), 7.52-7.47 (d, J=8.78 Hz, 1H), 7.05-6.99 (dd, J=8.96, 2.38 Hz, 1H), 3.80 (s, 3H), 3.21-3.13 (t, J=6.40 Hz, 2H), 3.11-3.01 (q, J=6.59 Hz, 2H), 2.87-2.75 (d, J=11.34 Hz, 2H), 2.30-2.18 (t, J=6.95 Hz, 2H), 1.94 (s, 3H), 1.88-1.73 (t, J=10.61 Hz, 2H), 1.70-1.45 (m, 5H), 1.30-1.10 (m, 2H)

LC-MS: 412.23 (M−H+)

Synthesis of Compound 41—[4-({[(5-bromo-6-hydroxy-1H-indazol-3-yl)carbonyl]amino}methyl) piperidin-1-yl] acetic acid To a solution of compound 20 (200 mg, 0.44 mmol) in CH₂Cl₂ (15 ml) cooled to −78° C. was slowly added a solution of 1M BBr₃ in CH₂Cl₂ (2.2 ml, 2.2 mmol) (about 1 h). The mixture was leaved to reach room temperature and stirred at this temperature for 2 days. The mixture was then poured in a saturated solution of NaHCO₃ and extracted with CH₂Cl₂ (3×100 ml). The basic phase was acidified with 1N HCl and concentrated at reduced pressure. The residue was then treated with DMSO (6 ml) and the [4-({[(5-bromo-6-hydroxy-1H-indazol-3-yl)carbonyl]amino}methyl)piperidin-1-yl]acetic acid 41 was purified using the following preparative HPLC parameters: channel A=CH₃CN+0.1% formic acid; channel B=H₂O+0.1% formic acid: flow=40 ml/min; gradient=10 to 45% of eluent A in 15 minutes. Yield 36 mg.

¹H NMR (300 MHz, DMSO-d6) δ=13.27 (br. s., 1H), 12.53-8.62 (m, OH), 8.39 (t, J=6.0 Hz, 1H), 8.27-8.14 (m, 1H), 7.08 (s, 1H), 6.74-3.42 (m, 2H), 3.34-3.07 (m, 6H), 2.62 (t, J=11.2 Hz, 2H), 1.74 (d, J=11.0 Hz, 3H), 1.42 (q, J=11.7 Hz, 2H)

Synthesis of Compound 42—[4-({[(5-bromo-6-methoxy-1H-indazol-3-yl)carbonyl]amino}methyl) piperidin-1-yl] acetic acid

[4-({[(5-bromo-6-methoxy-1H-indazol-3-yl)carbonyl] amino}methyl) piperidin-1-yl]acetic acid 42 was obtained by the purification step described in the preparation of compound 41. Yield 35 mg.

¹H NMR (300 MHz, DMSO-d6) δ=13.66 (br. s., 1H), 8.45 (t, J=6.1 Hz, 1H), 8.30 (s, 1H), 7.15 (s, 1H), 6.80-4.69 (m, 1H), 3.93 (s, 3H), 3.33-3.10 (m, 6H), 2.64 (t, J=11.2 Hz, 2H), 1.75 (d, J=10.9 Hz, 3H), 1.43 (q, J=11.6 Hz, 2H)

Synthesis of Compound 44—ethyl [4-({[(5-methoxy-1H-indazol-3-yl)carbonyl]amino}methyl) piperidin-1-yl]acetate Ethyl[4-({[(5-methoxy-1H-indazol-3-yl)carbonyl] amino}methyl) piperidin-1-yl]acetate was prepared, according to the procedure described for compound 25c, starting from 5-methoxy-N-(piperidin-4-ylmethyl)-1H-indazole-3-carboxamide hydrochloride 24b (65%).

¹H NMR (300 MHz, DMSO-d6) δ=13.54 (s, 1H), 8.30 (t, J=6.06 Hz, 1H), 7.56 (s, 1H), 7.51 (d, J=8.91 Hz, 1H), 7.05 (d, J=8.91 Hz, 1H), 4.00 (q, J=7.13 Hz, 2H), 3.81 (s, 3H), 3.34 (s, 2H), 3.17-3.24 (m, 2H), 2.81-2.95 (m, 4H), 1.50-1.75 (m, 3H), 1.16-1.36 (m, 2H), 1.11 (t, J=7.13 Hz, 3H)

LC-MS: 375.2 (M−H+)

The following Table 1A summarizes the chemical name and structure of the above described compounds 20-44.

TABLE 1A

| | IUPAC name | Structure |
|---|---|---|
| 20 | Ethyl [4-({[(5-bromo-6-methoxy-1H-indazol-3-yl)carbonyl]amino}methyl)piperidin-1-yl]acetate | 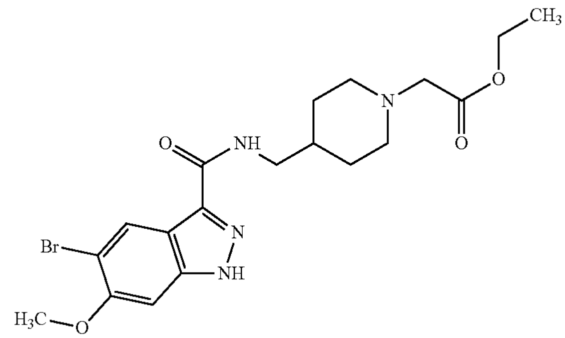 [SMILES: CCOC(=O)CN1CCC(CNC(=O)c2n[nH]c3cc(OC)c(Br)cc23)CC1] |
| 21 | {4-[({[6-methoxy-5-(pyridin-3-yl)-1H-indazol-3-yl]carbonyl}amino)methyl]piperidin-1-yl}acetic acid formiate hydrate | 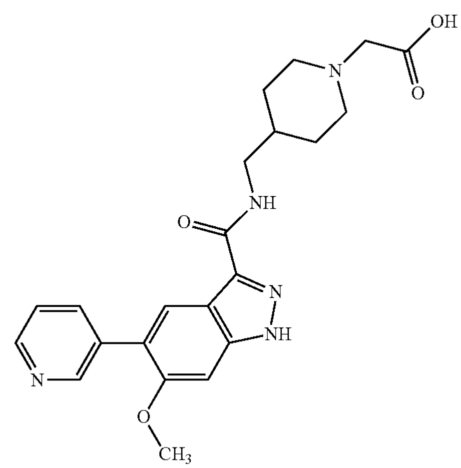 [SMILES: COc1cc2[nH]nc(C(=O)NCC3CCN(CC(=O)O)CC3)c2cc1-c1cccnc1] |
| 22 | {4-[({[6-methoxy-5-(5-methoxypyridin-3-yl)-1H-indazol-3-yl]carbonyl}amino)methyl]piperidin-1-yl}acetic acid hydrate | 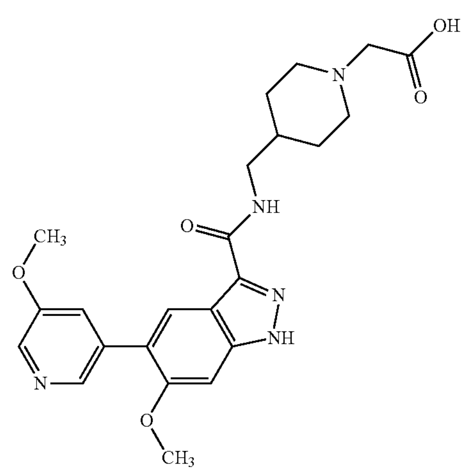 [SMILES: COc1cncc(-c2cc3c(C(=O)NCC4CCN(CC(=O)O)CC4)n[nH]c3cc2OC)c1] |

TABLE 1A-continued

| | IUPAC name | Structure |
|---|---|---|
| 23 | {4-[({[5-(2,3-difluorophenyl)-6-methoxy-1H-indazol-3-yl]carbonyl}amino)methyl]piperidin-1-yl}acetic acid hydrate | 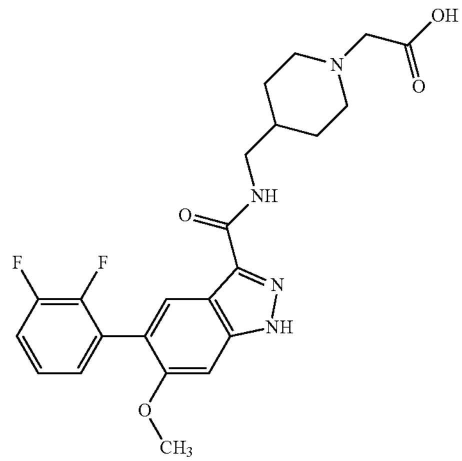 [SMILES: COc1cc2[nH]nc(C(=O)NCC3CCN(CC(=O)O)CC3)c2cc1-c1cccc(F)c1F] |
| 24 | 4-[4-({[(5-methoxy-1H-indazol-3-yl)carbonyl]amino}methyl)piperidin-1-yl]butanoic acid | 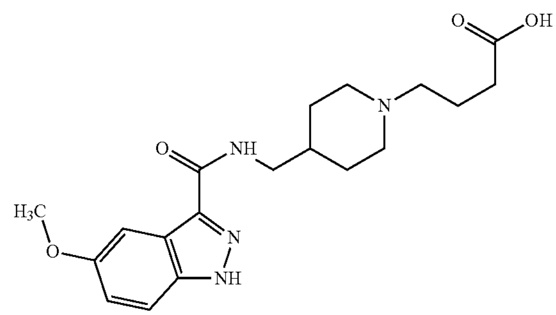 [SMILES: COc1ccc2[nH]nc(C(=O)NCC3CCN(CCCC(=O)O)CC3)c2c1] |
| 24c | Ethyl 4-[4-({[(5-methoxy-1H-indazol-3-yl)carbonyl]amino}methyl) piperidin-1-yl]butanoate | 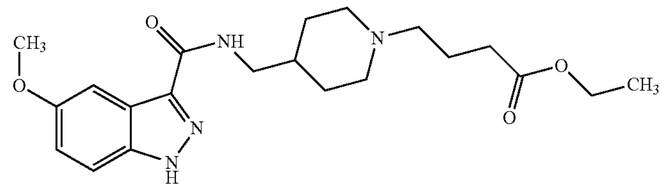 [SMILES: CCOC(=O)CCCN1CCC(CNC(=O)c2n[nH]c3ccc(OC)cc23)CC1] |
| 25 | {4-[({[5-(Pyrimidin-5-yl)-1H-indazol-3-yl]carbonyl}amino)methyl]piperidin-1-yl}acetic acid hydrate | 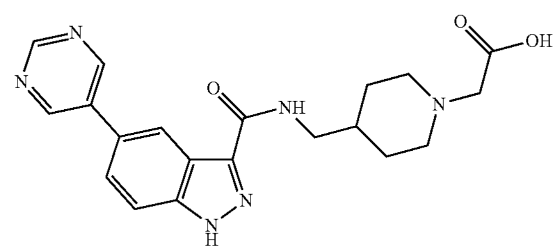 [SMILES: O=C(O)CN1CCC(CNC(=O)c2n[nH]c3ccc(-c4cncnc4)cc23)CC1] |
| 25c | Ethyl [4-({[(5-bromo-1H-indazol-3-yl)carbonyl]amino}methyl)piperidin-1-yl]acetate | 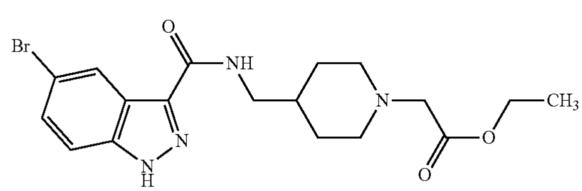 [SMILES: CCOC(=O)CN1CCC(CNC(=O)c2n[nH]c3ccc(Br)cc23)CC1] |

TABLE 1A-continued

| | IUPAC name | Structure |
|---|---|---|
| 26 | {4-[({[5-(3,5-Dimethylisoxazol-4-yl)-1H-indazol-3-yl]carbonyl}amino)methyl]piperidin-1-yl}acetic acid hydrate | 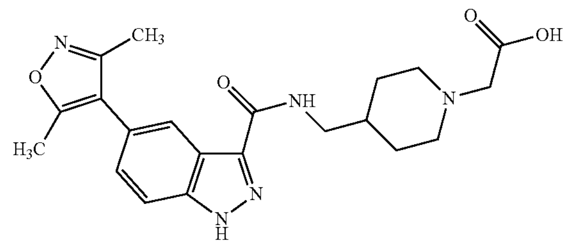 [SMILES: Cc1noc(C)c1-c1ccc2[nH]nc(C(=O)NCC3CCN(CC(=O)O)CC3)c2c1] |
| 27 | {4-[({[5-(2,3-dichlorophenyl)-1H-indazol-3-yl]carbonyl}amino)methyl]piperidin-1-yl}acetic acid hydrate | 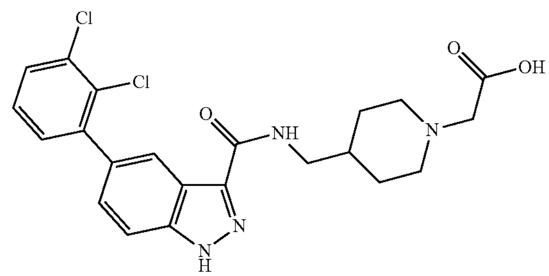 |
| 28 | {4-[({[5-(3-fluorophenyl)-1H-indazol-3-yl]carbonyl}amino)methyl]piperidin-1-yl}acetic acid hydrate | 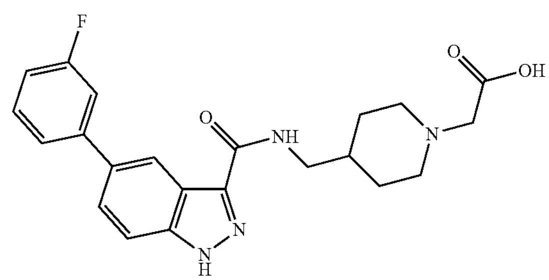 [SMILES: O=C(O)CN1CCC(CNC(=O)c2n[nH]c3ccc(-c4cccc(F)c4)cc23)CC1] |
| 29 | {4-[({[5-(2,3-difluorophenyl)-1H-indazol-3-yl]carbonyl}amino)methyl]piperidin-1-yl}acetic acid | 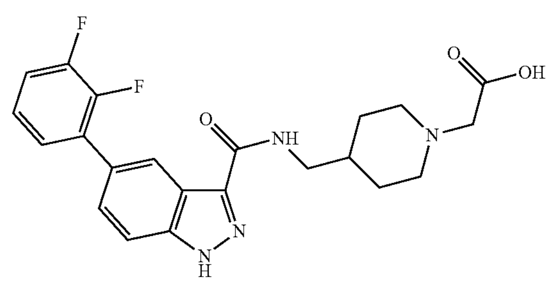 [SMILES: O=C(O)CN1CCC(CNC(=O)c2n[nH]c3ccc(-c4cccc(F)c4F)cc23)CC1] |
| 30 | {4-[({[5-(5-methoxypyridin-3-yl)-1H-indazol-3-yl]carbonyl}amino)methyl]piperidin-1-yl}acetic acid | 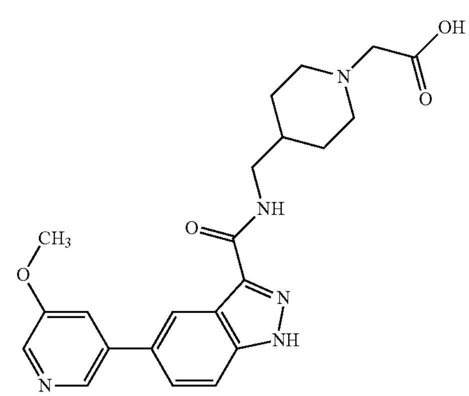 [SMILES: COc1cncc(-c2ccc3[nH]nc(C(=O)NCC4CCN(CC(=O)O)CC4)c3c2)c1] |

TABLE 1A-continued

| | IUPAC name | Structure |
|---|---|---|
| 31 | [4-({[(5-ethyl-1H-indazol-3-yl)carbonyl]amino}methyl)piperidin-1-yl]acetic acid | 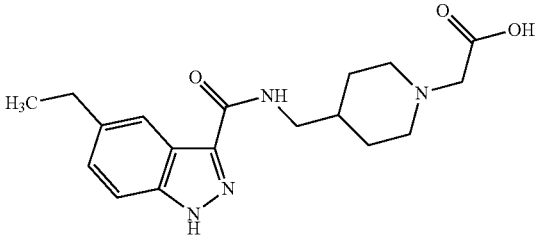 [SMILES: CCc1ccc2[nH]nc(C(=O)NCC3CCN(CC(=O)O)CC3)c2c1] |
| 32 | {4-[({[5-(propan-2-yl)-1H-indazol-3-yl]carbonyl}amino)methyl]piperidin-1-yl}acetic acid | 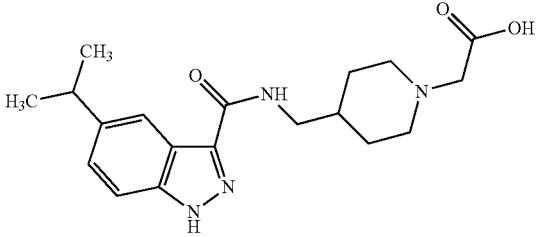 [SMILES: CC(C)c1ccc2[nH]nc(C(=O)NCC3CCN(CC(=O)O)CC3)c2c1] |
| 33 | {4-[({[5-(3,6-dihydro-2H-pyran-4-yl)-1H-indazol-3-yl]carbonyl}amino)methyl]piperidin-1-yl}acetic acid | 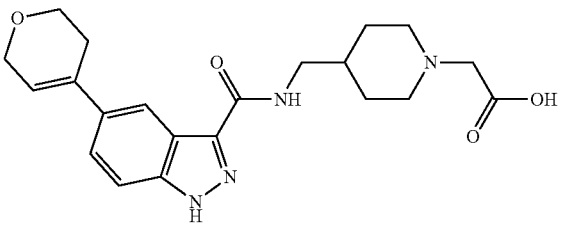 [SMILES: O=C(O)CN1CCC(CNC(=O)c2n[nH]c3ccc(C4=CCOCC4)cc23)CC1] |
| 34 | [4-({[(5-cyclohexyl-1H-indazol-3-yl)carbonyl]amino}methyl)piperidin-1-yl]acetic acid | 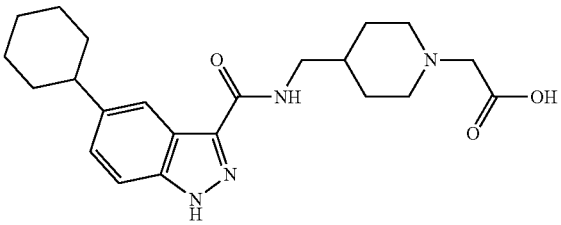 |
| 35 | [4-({[(5-pentyl-1H-indazol-3-yl)carbonyl]amino}methyl)piperidin-1-yl]acetic acid | 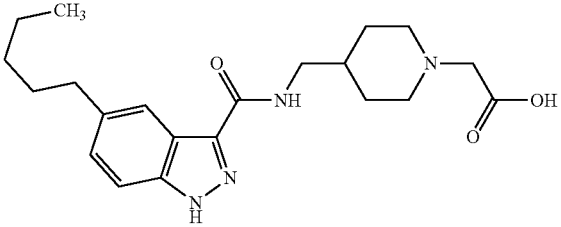 [SMILES: CCCCCc1ccc2[nH]nc(C(=O)NCC3CCN(CC(=O)O)CC3)c2c1] |
| 36 | 5-methoxy-N-[(1-{3-[(phenylcarbonyl)amino]propyl}piperidin-4-yl)methyl]-1H-indazole-3-carboxamide | 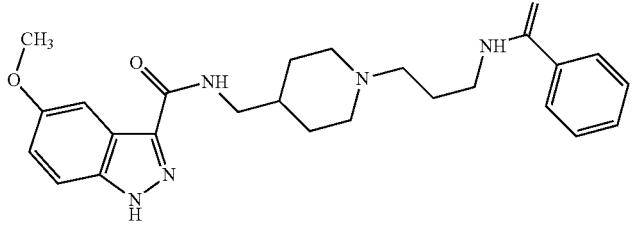 |

TABLE 1A-continued

| | IUPAC name | Structure |
|---|---|---|
| 37 | N-({1-[3-(butanoylamino)propyl]piperidin-4-yl}methyl)-5-methoxy-1H-indazole-3-carboxamide | 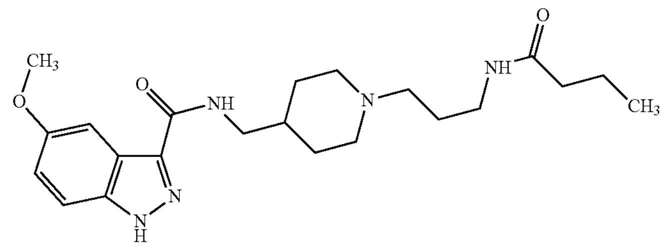 [SMILES: CCCC(=O)NCCCN1CCC(CNC(=O)c2n[nH]c3ccc(OC)cc23)CC1] |
| 38 | N-[(1-{3-[(2E)-but-2-enoylamino]propyl}piperidin-4-yl)methyl]-5-methoxy-1H-indazole-3-carboxamide | 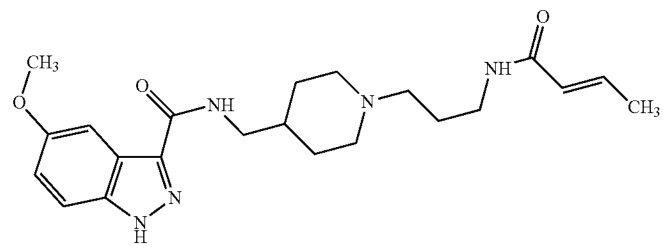 [SMILES: C/C=C/C(=O)NCCCN1CCC(CNC(=O)c2n[nH]c3ccc(OC)cc23)CC1] |
| 39 | 5-methoxy-N-({1-[3-(propanoylamino)propyl]piperidin-4-yl}methyl)-1H-indazole-3-carboxamide | 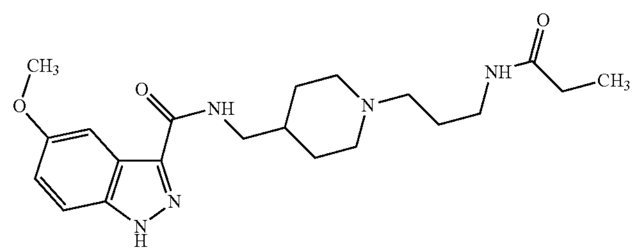 [SMILES: CCC(=O)NCCCN1CCC(CNC(=O)c2n[nH]c3ccc(OC)cc23)CC1] |
| 40 | N-({1-[3-(but-2-ynoylamino)propyl]piperidin-4-yl}methyl)-5-methoxy-1H-indazole-3-carboxamide | 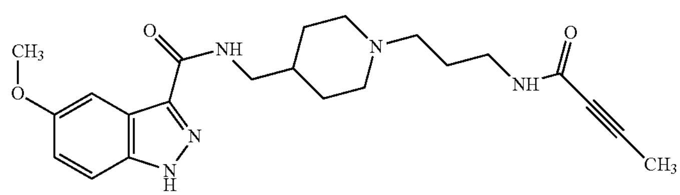 [SMILES: CC#CC(=O)NCCCN1CCC(CNC(=O)c2n[nH]c3ccc(OC)cc23)CC1] |
| 41 | [4-({[(5-bromo-6-hydroxy-1H-indazol-3-yl)carbonyl]amino}methyl)piperidin-1-yl]acetic acid | 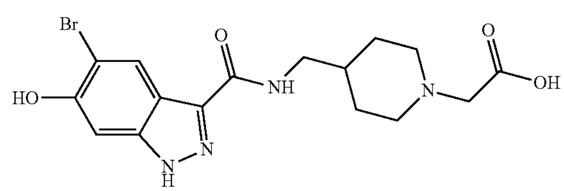 [SMILES: O=C(O)CN1CCC(CNC(=O)c2n[nH]c3cc(O)c(Br)cc23)CC1] |
| 42 | [4-({[(5-bromo-6-methoxy-1H-indazol-3-yl)carbonyl]amino}methyl)piperidin-1-yl]acetic acid | 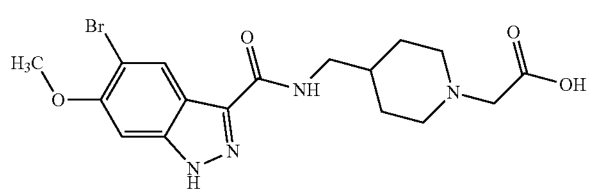 [SMILES: COc1cc2[nH]nc(C(=O)NCC3CCN(CC(=O)O)CC3)c2cc1Br] |
| 44 | ethyl [4-({[(5-methoxy-1H-indazol-3-yl)carbonyl]amino}methyl)piperidin-1-yl]acetate | 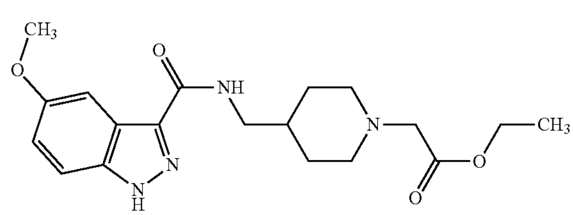 [SMILES: CCOC(=O)CN1CCC(CNC(=O)c2n[nH]c3ccc(OC)cc23)CC1] |

Pharmacological Properties

The pharmacological properties of the compounds of formula (I) useful in the present invention were evaluated by the methods described in the following sections.

Test I—Activity on Human GSK-3β (Test In Vitro)

Activity on human GSK-3β was assessed using the following methods (according to Meijer et al., Chem. Biol., 2003-10:1255-1266).

In a first screening assay, compounds were tested in duplicate at a concentration of 10 μM.

Human recombinant enzyme GSK-3β was incubated for 90 minutes at 22° C. in the presence of compounds or vehicle in a reaction buffer containing ATP plus 100 nM unphosphorylated specific substrate peptide (Ulight-CFFKNIVTPRTPPPSQGK-amide). Substrate phosphorylation was measured by LANCE technology (PerkinElmer, Conn., USA).

The results, reported in the following Table 4, are expressed as a percentage of inhibition of control specific activity obtained in the presence of the test compounds (as % inhibition at 10 μM).

In a second assay, the same compounds were assayed at five concentrations ranging from 100 μM to 10 nM with ten-fold dilutions in duplicate. Compounds 1 to 15 were tested using the same first assay, compounds 16 to 41 were tested in another assay based on the binding and displacement of AlexaFluor® 647 labeled, ATP-competitive Kinase inhibitor scaffold using LanthaScreen™ TR-FRET technology Eu Kinase assay packet according to manufacturer's instruction (Life Technologies, Italy). The results of the two assays are comparable.

The $IC_{50}$ values (concentration causing a half maximal inhibition of control specific activity), reported in table 4, were determined by non-linear regression analysis of the inhibition curves generated with mean replicate values using Hill equation curve fitting.

TABLE 4

| Compound N° | % Inhibition [10 μM] | $IC_{50}$ [μM] |
|---|---|---|
| 1 | 92 | 0.67 |
| 2 | 85 | 0.87 |
| 3 | 94 | 0.69 |
| 4 | — | 0.03 |
| 5 | — | 0.05 |
| 6 | — | 0.07 |
| 7 | — | 0.06 |
| 8 | — | 0.02 |
| 9 | — | 0.20 |
| 10 | — | 0.03 |

TABLE 4-continued

| Compound N° | % Inhibition [10 μM] | $IC_{50}$ [μM] |
|---|---|---|
| 11 | — | 0.89 |
| 12 | — | 0.56 |
| 13 | — | 0.56 |
| 14 | — | 1.40 |
| 15 | — | 0.05 |
| 16 | — | 0.58 |
| 18 | — | 1.06 |
| 24 | — | 1.03 |
| 25 | — | 0.22 |
| 25b | — | 0.53 |
| 26 | — | 0.91 |
| 27 | — | 0.10 |
| 28 | — | 0.11 |
| 29 | — | 0.03 |
| 30 | — | 0.02 |
| 31 | — | 0.96 |
| 32 | — | 3.91 |
| 33 | — | 1.04 |
| 34 | — | 1.07 |
| 35 | — | 2.04 |
| 36 | — | 3.42 |
| 37 | — | 0.97 |
| 38 | — | 0.78 |
| 39 | — | 0.95 |
| 40 | — | 0.88 |
| 41 | 71 | — |

The results showed that the compounds according to the present invention had good inhibitory activity in this assay: at 10 μM the % of inhibition is greater than 70% and the $IC_{50}$ is obtained with less than 4.00 μM of each compound. Most compounds showed an IC50 value lower than 1.50 μM.

Test II—Selectivity on GSK-3β (Test In Vitro)

(a) Compounds 1 and 2 were tested against a panel of 60 kinases in order to assess their selectivity. The assays were chosen taking into consideration the diversity of assay families.

Tested kinases were representative of following kinase sub-families:
protein-serine/threonine kinases;
protein-tyrosine kinases;
other kinases; and
atypical kinases.

Human recombinant kinases were incubated in the presence of specific peptide substrates plus ATP for different times (10, 15, 30, 60 or 90 minutes) at 22° C. Phosphorylated substrate was detected by LANCE or HTRF technology (CISBIO, MA, USA). The compounds were tested at 10 μM in duplicate.

The results are expressed as a percentage of inhibition of control specific activity obtained in the presence of the test compounds and are reported in the following Table 5.

TABLE 5

| Kinase Family | Kinase Sub-Family | Assay | % inhibition of control values | |
|---|---|---|---|---|
| | | | compound 1 | compound 2 |
| Protein-tyrosine kinases | RTK | c-Met kinase (h) | 3 | 0 |
| | RTK | EphA4 kinase (h) | 0 | 0 |
| | RTK | EphB2 kinase (h) | 4 | 7 |
| | RTK | EphB4 kinase (h) | 2 | 17 |
| | RTK | FGFR1 kinase (h) | 0 | 0 |
| | RTK | FGFR4 kinase (h) | 0 | 0 |
| | RTK | IGF1R kinase (h) | 0 | 0 |
| | RTK | IRK (h) (InsR) | 0 | 0 |
| | RTK | Ret kinase (h) | 0 | 0 |
| | RTK | TRKA (h) | 1 | 0 |

TABLE 5-continued

| Kinase Family | Kinase Sub-Family | Assay | % inhibition of control values | |
|---|---|---|---|---|
| | | | compound 1 | compound 2 |
| | CTK | Abl kinase (h) | 0 | 0 |
| | CTK | JAK1 (h) | 0 | 0 |
| | CTK | JAK2 (h) | 0 | 0 |
| | CTK | Fyn kinase (h) | 0 | 3 |
| | CTK | Src kinase (h) | 1 | 6 |
| Protein serine/threonine kinases | CMGC | GSK3beta (h) | 94 | 90 |
| | CMGC | DYRK1a (h) | 76 | 56 |
| | CMGC | PCTAIRE1 kinase (h) | 22 | 71 |
| | CMGC | CDC2/CDK1 (h) (cycB) | 7 | 0 |
| | CMGC | CDK2 (h) (cycA) | 18 | 11 |
| | CMGC | CDK5/p35 (h) | 19 | 13 |
| | CMGC | ERK1 (h) | 20 | 15 |
| | CMGC | ERK2 (h) (P42mapk) | 58 | 46 |
| | CMGC | p38alpha kinase (h) | 0 | 0 |
| | CMGC | p38gamma kinase (h) | 0 | 0 |
| | CMGC | p38delta kinase (h) | 0 | 0 |
| | CaMK | CHK1 (h) | 5 | 8 |
| | CaMK | AMPKalpha | 16 | 19 |
| | CaMK | CaMK4 (h) | 0 | 0 |
| | CaMK | DAPK1 (h) | 22 | 12 |
| | CaMK | DCAMKL1 (h) | 0 | 3 |
| | CaMK | Pim2 kinase (h) | 3 | 4 |
| | CaMK | MAPKAPK2 (h) | 0 | 0 |
| | CaMK | MNK2 (h) | 0 | 0 |
| | CaMK | PhKgamma 2 (h) | 30 | 1 |
| | CaMK | Pim1 kinase (h) | 0 | 2 |
| | CaMK | smMLCK (h) (MYLK) | 0 | 8 |
| | AGC | GRK3/BARK2 (h) (ADRBK2) | 0 | 0 |
| | AGC | Akt1/PKBalpha (h) | 0 | 4 |
| | AGC | MSK1 (h) | 7 | 16 |
| | AGC | PDK1 (h) | 6 | 6 |
| | AGC | RSK2 (h) | 0 | 1 |
| | AGC | PKA (h) | 0 | 2 |
| | AGC | PKCalpha (h) | 0 | 0 |
| | AGC | PKCbeta 1 (h) | 0 | 1 |
| | AGC | PKCgamma (h) | 3 | 0 |
| | CK1 | CK1alpha (h) | 0 | 12 |
| | STE | PAK1 (h) | 1 | 0 |
| | STE | HGK (h) (MAP4K4) | 8 | 23 |
| | STE | MEK1/MAP2K1 (h) | 24 | 9 |
| | STE | TAOK2 (TAO1) (h) | 3 | 26 |
| | TKL | DLK1 (h) (MAP3K12) | 0 | 0 |
| | TKL | IRAK4 (h) | 0 | 8 |
| Other kinases | — | IKKalpha (h) | 0 | 0 |
| | — | IKKepsilon (h) (IKBKE) | 0 | 0 |
| | — | MYT1 kinase (h) | 0 | 1 |
| | — | NEK1 (h) | 0 | 0 |
| | — | NEK7 (h) | 0 | 0 |
| | — | AurA/Aur2 kinase (h) | 7 | 1 |
| | — | AurB/Aur1 kinase (h) | 0 | 6 |
| Atypical kinases | — | mTOR kinase (h) (FRAP1) | 2 | 2 |

Results confirmed that both the tested compounds have an inhibitory activity on GSK-3β and that they have higher affinity to GSK-3β when compared to the other kinases, showing a good selectivity profile.

(b) Compounds 3, 8, 29 and 31 were tested against the same panel of 60 kinases under the same conditions described above for compounds 1 and 2.

The results are expressed as a percent of inhibition of control specific activity obtained in the presence of the test compounds and are reported in the following Table 6.

TABLE 6

| Kinase Family | Kinase Sub-Family | Assay | Compound 3 | Compound 8 | Compound 29 | Compound 31 |
|---|---|---|---|---|---|---|
| Protein-tyrosine kinases | RTK | c-Met kinase (h) | 0 | 7 | — | — |
| | RTK | EphA4 kinase (h) | 0 | 0 | — | — |
| | RTK | EphB2 kinase (h) | 0 | 2 | — | — |

TABLE 6-continued

| Kinase Family | Kinase Sub-Family | Assay | Compound 3 | Compound 8 | Compound 29 | Compound 31 |
|---|---|---|---|---|---|---|
| | RTK | EphB4 kinase (h) | 0 | 0 | — | — |
| | RTK | FGFR1 kinase (h) | 0 | 8 | — | — |
| | RTK | FGFR4 kinase (h) | 0 | 2 | — | — |
| | RTK | IGF1R kinase (h) | 0 | 3 | — | — |
| | RTK | IRK (h) (InsR) | 0 | 9 | 0 | 0 |
| | RTK | Ret kinase (h) | 0 | 0 | — | — |
| | RTK | TRKA (h) | 0 | 14 | 3 | 0 |
| | CTK | Abl kinase (h) | 0 | 0 | — | — |
| | CTK | JAK1 (h) | 4 | 7 | — | — |
| | CTK | JAK2 (h) | 0 | 23 | — | — |
| | CTK | Fyn kinase (h) | 0 | 0 | — | — |
| | CTK | Src kinase (h) | 0 | 0 | 0 | 9 |
| Protein serine/threonine kinases | CMGC | GSK3beta (h) | 89 | 99 | 100 | 89 |
| | CMGC | DYRK1a (h) | 51 | 99 | 100 | 77 |
| | CMGC | PCTAIRE1 kinase (h) | 0 | 84 | 49 | 27 |
| | CMGC | CDC2/CDK1 (h) (cycB) | 8 | 80 | 80 | 10 |
| | CMGC | CDK2 (h) (cycA) | 21 | 92 | 77 | 35 |
| | CMGC | CDK5/p35 (h) | 9 | 77 | 77 | 16 |
| | CMGC | ERK1 (h) | 19 | 66 | 61 | 1 |
| | CMGC | ERK2 (h) (P42mapk) | 34 | 74 | 67 | 9 |
| | CMGC | p38alpha kinase (h) | 0 | 1 | — | — |
| | CMGC | p38gamma kinase (h) | — | — | — | — |
| | CMGC | p38delta kinase (h) | 0 | 18 | — | — |
| | CaMK | CHK1 (h) | 0 | 0 | — | — |
| | CaMK | AMPKalpha | 5 | 68 | — | — |
| | CaMK | CaMK4 (h) | 15 | 4 | — | — |
| | CaMK | DAPK1 (h) | 3 | 47 | — | — |
| | CaMK | DCAMKL1 (h) | 0 | 0 | — | — |
| | CaMK | Pim2 kinase (h) | 0 | 0 | — | — |
| | CaMK | MAPKAPK2 (h) | 0 | 17 | — | — |
| | CaMK | MNK2 (h) | 3 | 4 | — | — |
| | CaMK | PhKgamma 2 (h) | 1 | 0 | — | — |
| | CaMK | Pim1 kinase (h) | 12 | 17 | — | — |
| | CaMK | smMLCK (h) (MYLK) | — | — | 17 | 1 |
| | AGC | GRK3/BARK2 (h) (ADRBK2) | 0 | 8 | — | — |
| | AGC | Akt1/PKBalpha (h) | 0 | 0 | — | — |
| | AGC | MSK1 (h) | — | — | — | — |
| | AGC | PDK1 (h) | 0 | 0 | — | — |
| | AGC | RSK2 (h) | 4 | 4 | — | — |
| | AGC | PKA (h) | 0 | 0 | — | — |
| | AGC | PKCalpha (h) | 5 | 19 | — | — |
| | AGC | PKCbeta 1 (h) | 0 | 28 | — | — |
| | AGC | PKCgamma (h) | 2 | 0 | — | — |
| | CK1 | CK1alpha (h) | 0 | 6 | — | — |
| | STE | PAK1 (h) | 0 | 3 | — | — |
| | STE | HGK (h) (MAP4K4) | 3 | 72 | 71 | 10 |
| | STE | MEK1/MAP2K1 (h) | — | — | 75 | 9 |
| | STE | TAOK2 (TAO1) (h) | 0 | 79 | 61 | 9 |
| | TKL | DLK1 (h) (MAP3K12) | 0 | 58 | — | — |
| | TKL | IRAK4 (h) | 0 | 0 | — | — |
| Other kinases | — | IKKalpha (h) | 0 | 1 | — | — |
| | — | IKKepsilon (h) (IKBKE) | 0 | 3 | — | — |
| | — | MYT1 kinase (h) | 2 | 20 | — | — |
| | — | NEK1 (h) | — | — | 9 | 0 |
| | — | NEK7 (h) | 2 | 0 | — | — |
| | — | AurA/Aur2 kinase (h) | 4 | 10 | — | — |
| | — | AurB/Aur1 kinase (h) | 0 | 0 | — | — |
| Atypical kinases | — | mTOR kinase (h) (FRAP1) | — | — | — | — |

Results confirmed that also compounds 3 and 31 had an inhibitory activity on GSK-3β and higher affinity to GSK-3β when compared to all other kinases, showing a good selectivity profile, and that compounds 8 and 29 had an inhibitory activity on GSK-3β and good affinity to GSK-3β when compared to most of other kinases of the same family and to the kinases of different families.

The invention claimed is:

1. A method of treatment of a pathological state arising from the uncontrolled activation and/or over-expression of GSK-3β, selected from the group consisting of (i) a mood disorder; (ii) a schizophrenic disorder; and comprising administering to a human being in need thereof an effective amount of a 1H-indazole-3-carboxamide of formula (I):

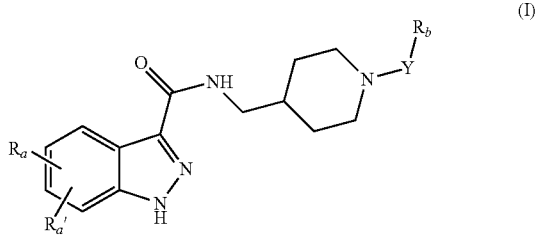

wherein
$R_a$ and $R_a'$ are the same or different and each is independently:
  a hydrogen atom;
  a halogen atom;
  a hydroxy group;
  a $C_1$-$C_6$ alkyl, $C_2$-$C_6$ alkenyl, $C_2$-$C_6$ alkynyl or $C_1$-$C_6$ alkoxy group, optionally substituted by one or more substituents selected from the group consisting of halogen, hydroxy, —$NH_2$, and $C_1$-$C_3$ alkoxy; or
  a carbocyclic or heterocyclic ring, aliphatic or aromatic, having from 3 to 12 members, optionally substituted by one or more substituents selected from the group consisting of halogen, hydroxy, $C_1$-$C_6$ alkyl, $C_1$-$C_6$ alkoxy, —$NR_1R_2$, —C(O)OH, —C(O)OR_1, and —C(O)NR_1R_2;
Y is a bond or a $C_1$-$C_6$ alkyl, $C_2$-$C_6$ alkenyl, or $C_2$-$C_6$ alkynyl group, optionally substituted by one or more substituents selected from the group consisting of halogen, hydroxy, —$NH_2$, and $C_1$-$C_3$ alkoxy;
$R_b$ is a $C_1$-$C_6$ alkoxy group, —C(O)OH, —C(O)OR_1, —$NO_2$, or —NHC(O)R_1;
$R_1$ and $R_2$ are the same or different and each is independently a hydrogen atom, a $C_1$-$C_4$ alkyl group, a $C_2$-$C_4$ alkenyl group, a $C_2$-$C_4$ alkynyl group, or a phenyl group;
or an addition salt with a pharmaceutically acceptable acid or base.

2. A method according to claim 1, wherein
$R_a$ and $R_a'$ are the same or different and each is independently:
  a hydrogen atom;
  a halogen atom, selected from the group consisting of chlorine, bromine and iodine;
  a hydroxy group;
  a $C_1$-$C_6$ alkyl or $C_1$-$C_6$ alkoxy group, optionally substituted by one or more substituents selected from the group consisting of halogen, hydroxy, —$NH_2$, and $C_1$-$C_3$ alkoxy; or
  a carbocyclic or heterocyclic ring, saturated or unsaturated, having from 4 to 10 members, optionally substituted by one or more substituents selected from the group consisting of halogen, hydroxy, $C_1$-$C_6$ alkyl, $C_1$-$C_6$ alkoxy, —$NR_1R_2$, —C(O)OH, —C(O)OR_1, and —C(O)NR_1R_2; and
$R_1$ and $R_2$ are the same or different and each is independently a hydrogen atom, a $C_1$-$C_4$ alkyl group, a $C_2$-$C_4$ alkenyl group, a $C_2$-$C_4$ alkynyl group, or a phenyl group.

3. A method according to claim 2, wherein
$R_a$ and $R_a'$ are the same or different and each is independently:
  a halogen atom, selected from the group consisting of chlorine and bromine;
  a hydroxy group;
  a $C_1$-$C_6$ alkyl group;
  a $C_1$-$C_6$ alkoxy group;
  or a carbocyclic or heterocyclic ring, saturated or unsaturated, having from 5 to 6 members, optionally substituted by one or more substituents, selected from the group consisting of halogen, hydroxy, $C_1$-$C_6$ alkyl, $C_1$-$C_6$ alkoxy, —$NR_1R_2$, and —COOH; and
$R_1$ and $R_2$ are the same or different and each is independently a hydrogen atom, a $C_1$-$C_4$ alkyl group, a $C_2$-$C_4$ alkenyl group, a $C_2$-$C_4$ alkynyl group, or a phenyl group.

4. A method according to claim 3, wherein
$R_a$ and $R_a'$ are the same or different and each is independently:
  a bromine atom;
  a hydroxy group;
  a $C_1$-$C_3$ alkoxy group; or
  an unsaturated carbocyclic or heterocyclic ring, having 6 members, optionally substituted by one or two substituents selected from the group consisting of halogen, hydroxy, $C_1$-$C_3$ alkyl, $C_1$-$C_3$ alkoxy, —$NR_1R_2$, and —COOH; and
$R_1$ and $R_2$ are the same or different and each is independently a hydrogen atom, a $C_1$-$C_a$ alkyl group, a $C_2$-$C_4$ alkenyl group, a $C_2$-$C_4$ alkynyl group, or a phenyl group.

5. A method according to claim 1, wherein Y is a bond or $C_1$-$C_6$ alkyl group, optionally substituted by one or more substituents selected from the group consisting of halogen, hydroxy, —$NH_2$, and $C_1$-$C_3$ alkoxy.

6. A method according to claim 5, wherein Y is a $C_1$-$C_6$ alkyl group.

7. A method according to claim 6, wherein Y is a $C_1$-$C_3$ alkyl group.

8. A method according to claim 1, wherein $R_b$ is a $C_1$-$C_6$ alkoxy group, —C(O)OH, —C(O)OR_1, or —NHCOR_1.

9. A method according to claim 8, wherein $R_b$ is a $C_1$-$C_6$ alkoxy group or —C(O)OH.

10. A method according to claim 9, wherein $R_b$ is a $C_1$-$C_3$ alkoxy group or —C(O)OH.

11. A method of treatment according to claim 1, wherein $R_1$ and $R_2$ are the same or different and each is independently a $C_1$-$C_3$ alkyl group.

12. A method according to claim 1, wherein said pathological state is a mood disorder selected from the group consisting of a bipolar disorder and a depressive disorder.

13. A method according to claim 12, wherein said bipolar disorder is selected from the group consisting of bipolar I, bipolar II, cyclothymia, and bipolar disorder not otherwise specified (BD-NOS).

14. A method according to claim 12, wherein said depressive disorder is selected from the group consisting of major depressive disorder (MDD), atypical depression (AD), melancholic depression, psychotic major depression (PMD), catatonic depression, postpartum depression (PPD), seasonal affective disorder (SAD), dysthymia, and depressive disorder not otherwise specified (DD-NOS).

15. A method according to claim 1, wherein said pathological state is schizophrenia.

* * * * *